(12) United States Patent
Green et al.

(10) Patent No.: US 8,653,088 B2
(45) Date of Patent: *Feb. 18, 2014

(54) COMPOSITIONS USEFUL AS INHIBITORS OF PROTEIN KINASES

(75) Inventors: Jeremy Green, Waltham, MA (US); Ronald Grey, Jr., Attleboro, MA (US); Albert Pierce, Cambridge, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 513 days.

This patent is subject to a terminal disclaimer.

(21) Appl. No.: 12/552,003

(22) Filed: Sep. 1, 2009

(65) Prior Publication Data

US 2009/0325968 A1 Dec. 31, 2009

Related U.S. Application Data

(62) Division of application No. 10/772,219, filed on Feb. 4, 2004, now Pat. No. 7,601,718.

(60) Provisional application No. 60/445,529, filed on Feb. 6, 2003.

(51) Int. Cl.
*A01N 43/90* (2006.01)
*A61K 31/52* (2006.01)
*C07D 473/00* (2006.01)

(52) U.S. Cl.
USPC .................. 514/263.1; 514/262.1; 544/264

(58) Field of Classification Search
USPC .................. 544/264; 514/263.1, 262.1, 264
See application file for complete search history.

(56) References Cited

U.S. PATENT DOCUMENTS

| | | | |
|---|---|---|---|
| 3,133,081 A | 5/1964 | Lafferty | |
| 3,755,322 A | 8/1973 | Winter et al. | |
| 3,935,183 A | 1/1976 | Baron et al. | |
| 3,998,951 A | 12/1976 | Harnish et al. | |
| 4,004,009 A | 1/1977 | Anderson | |
| 4,051,252 A | 9/1977 | Mayer et al. | |
| 4,493,726 A | 1/1985 | Burdeska et al. | |
| 4,540,698 A | 9/1985 | Ishikawa et al. | |
| 4,711,951 A | 12/1987 | Axen et al. | |
| 5,124,441 A | 6/1992 | Carlsson et al. | |
| 5,710,158 A | 1/1998 | Myers et al. | |
| 5,916,908 A | 6/1999 | Giese et al. | |
| 5,972,946 A | 10/1999 | Murata et al. | |
| 6,093,716 A | 7/2000 | Davis et al. | |
| 6,184,226 B1 | 2/2001 | Chakravarty et al. | |
| 6,200,977 B1 | 3/2001 | Cushing et al. | |
| 6,277,989 B1 | 8/2001 | Chakravarty et al. | |
| 6,342,601 B1 | 1/2002 | Bantick et al. | |
| 6,495,582 B1 | 12/2002 | Hale et al. | |
| 6,528,509 B1 | 3/2003 | Hale et al. | |
| 6,528,513 B2 | 3/2003 | Cushing et al. | |
| 6,558,657 B1 | 5/2003 | Mandeville, III et al. | |
| 6,562,971 B2 | 5/2003 | Frauenkron et al. | |
| 6,579,983 B1 | 6/2003 | Batchelor et al. | |
| 6,589,958 B1 | 7/2003 | Frietze | |
| 6,593,326 B1 | 7/2003 | Bradbury et al. | |
| 6,610,677 B2 | 8/2003 | Davies et al. | |
| 6,613,776 B2 | 9/2003 | Knegtel et al. | |
| 6,638,926 B2 | 10/2003 | Davies et al. | |
| 6,642,227 B2 | 11/2003 | Cao et al. | |
| 6,653,300 B2 | 11/2003 | Bebbington et al. | |
| 6,653,301 B2 | 11/2003 | Bebbington et al. | |
| 6,656,939 B2 | 12/2003 | Bebbington et al. | |
| 6,660,731 B2 | 12/2003 | Bebbington et al. | |
| 6,664,247 B2 | 12/2003 | Bebbington et al. | |
| 6,689,778 B2 | 2/2004 | Bemis et al. | |
| 6,696,452 B2 | 2/2004 | Davies et al. | |
| 6,727,251 B2 | 4/2004 | Bebbington et al. | |

(Continued)

FOREIGN PATENT DOCUMENTS

DE 2458965 6/1976
EP 0019811 12/1980

(Continued)

OTHER PUBLICATIONS

Patel et al., "Synthesis and Biological Activity of Substituted 1,4,5,6-tetrahydropyridazin-4-ones, 5,6-dihydro-3-hydroxy-1H-pyrazolo[4,3-c]pyridazines and 2,8-dihydro-1H-pyrano[2,3-d]pyridazines", Indian Journal of Chemistry, vol. 28B, pp. 733-744, Sep. 1989.
Ghozlan et al., "Synthesis of Polyfunctionally Substituted Pyridazines", Liebigs Ann. Chem., pp. 293-296, 1990.
Ghozlan et al., "Reactions with 3-oxo-2-phenylhydrazonobutyronitrile: New Routes for the Synthesis of Pyridazines" Gazzetta Chimica Italiana, vol. 119, pp. 95-97, 1989.
Witherington et al., "5-Aryl-pyrazolo[3,4-b]pyridazines: Potent Inhibitors of Glycogen Synthase Kinase-3 (GSK-3)", Bioorganic & Medical Chemistry Letters, vol. 13, pp. 1581-1584, 2003.
Jambhekar, S.S., "Biopharmaceutical Properties of Drug Substances" in Principles of Medicinal Chemistry, 4th ed., 12-24, (1995).
Layzer, R.B., "Section Five—Degenerative Diseases of the Nervous System" in Cecil Textbook of Medicine, 20th ed., 2: 2050-2057 (1996).
Lee, S.J. et al., "Discovery of Potent Cyclic GMP Phosphodiesterase Inhibitors. 2-Pyridyl- and 2-Imidazolylquinazolines Possessing Cyclic Gmp Phosphodiesterase and Thromboxane Synthesis Inhibitory Activities," J. Med. Chem., 38 (18): 3547-3557 (1995).

(Continued)

*Primary Examiner* — Paul V. Ward
(74) *Attorney, Agent, or Firm* — Rory C. Stewart

(57) ABSTRACT

The present invention provides a compound of formula I:

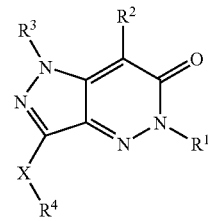

I or a pharmaceutically acceptable salt or mixtures thereof. These compounds are inhibitors of protein kinases, particularly inhibitors of GSK mammalian protein kinase, and more particularly inhibitors of GSK-3 mammalian protein kinase. The invention also provides pharmaceutically acceptable compositions comprising the compounds of the invention and methods of utilizing those compounds and compositions in the treatment of various protein kinase mediated disorders.

25 Claims, No Drawings

(56) References Cited

U.S. PATENT DOCUMENTS

| | | |
|---|---|---|
| 6,743,791 B2 | 6/2004 | Cao et al. |
| 6,825,190 B2 | 11/2004 | Moon et al. |
| 6,838,464 B2 | 1/2005 | Pease et al. |
| 6,841,579 B1 | 1/2005 | Plowman et al. |
| 6,846,928 B2 | 1/2005 | Bebbington et al. |
| 6,884,804 B2 | 4/2005 | Choon-Moon |
| 6,949,544 B2 | 9/2005 | Bethiel et al. |
| 6,989,385 B2 | 1/2006 | Bebbington et al. |
| 7,008,948 B2 | 3/2006 | Bebbington et al. |
| 7,084,159 B2 | 8/2006 | Cao et al. |
| 7,087,603 B2 | 8/2006 | Bebbington et al. |
| 7,091,343 B2 | 8/2006 | Bebbington et al. |
| 7,098,330 B2 | 8/2006 | Bebbington et al. |
| 7,115,739 B2 | 10/2006 | Bebbington et al. |
| 7,179,826 B2 | 2/2007 | Bebbington et al. |
| 7,253,187 B2 | 8/2007 | Cao et al. |
| 7,304,061 B2 | 12/2007 | Hale et al. |
| 7,345,054 B2 | 3/2008 | Hale et al. |
| 7,361,665 B2 | 4/2008 | Ledeboer et al. |
| 7,390,815 B2 | 6/2008 | Davies et al. |
| 7,427,681 B2 | 9/2008 | Bebbington et al. |
| 7,473,691 B2 | 1/2009 | Davies et al. |
| 7,491,730 B2 | 2/2009 | Forster et al. |
| 7,528,142 B2 | 5/2009 | Binch et al. |
| 7,531,536 B2 | 5/2009 | Bebbington et al. |
| 7,557,106 B2 | 7/2009 | Charrier et al. |
| 7,579,349 B2 | 8/2009 | Nowak et al. |
| 7,601,718 B2 * | 10/2009 | Green et al. .......... 514/250 |
| 7,625,913 B2 | 12/2009 | Bebbington et al. |
| 7,691,853 B2 | 4/2010 | Bebbington et al. |
| 7,737,151 B2 | 6/2010 | Mortimore et al. |
| 7,767,672 B2 | 8/2010 | Binch et al. |
| 7,820,685 B2 | 10/2010 | Binch et al. |
| 7,863,282 B2 | 1/2011 | Bebbington et al. |
| 7,872,129 B2 | 1/2011 | Forster et al. |
| 7,951,820 B2 | 5/2011 | Bebbington et al. |
| 7,982,037 B2 | 7/2011 | Bebbington et al. |
| 7,989,456 B2 | 8/2011 | Mortimore et al. |
| 2001/0018436 A1 | 8/2001 | Cushing et al. |
| 2002/0052386 A1 | 5/2002 | Armistead et al. |
| 2002/0065270 A1 | 5/2002 | Moriarty et al. |
| 2003/0004161 A1 | 1/2003 | Bebbington et al. |
| 2003/0004164 A1 | 1/2003 | Bebbington et al. |
| 2003/0022885 A1 | 1/2003 | Bebbington et al. |
| 2003/0036543 A1 | 2/2003 | Bebbington et al. |
| 2003/0055044 A1 | 3/2003 | Davies et al. |
| 2003/0055068 A1 | 3/2003 | Bebbington et al. |
| 2003/0064981 A1 | 4/2003 | Knegtel et al. |
| 2003/0064982 A1 | 4/2003 | Davies et al. |
| 2003/0069239 A1 | 4/2003 | Cai et al. |
| 2003/0069248 A1 | 4/2003 | Chakravarty et al. |
| 2003/0073687 A1 | 4/2003 | Bebbington et al. |
| 2003/0078166 A1 | 4/2003 | Davies et al. |
| 2003/0078275 A1 | 4/2003 | Bebbington et al. |
| 2003/0083327 A1 | 5/2003 | Davies et al. |
| 2003/0087922 A1 | 5/2003 | Bethiel et al. |
| 2003/0092714 A1 | 5/2003 | Cao et al. |
| 2003/0096813 A1 | 5/2003 | Cao et al. |
| 2003/0096816 A1 | 5/2003 | Cao et al. |
| 2003/0105090 A1 | 6/2003 | Bebbington et al. |
| 2003/0144309 A1 | 7/2003 | Choon-Moon |
| 2003/0171389 A1 | 9/2003 | Bemis et al. |
| 2003/0187002 A1 | 10/2003 | Mortlock et al. |
| 2003/0199526 A1 | 10/2003 | Choquette et al. |
| 2003/0207873 A1 | 11/2003 | Harrington |
| 2003/0225073 A1 | 12/2003 | Bebbington et al. |
| 2004/0002496 A1 | 1/2004 | Bebbington et al. |
| 2004/0009974 A1 | 1/2004 | Bebbington et al. |
| 2004/0009981 A1 | 1/2004 | Bebbington et al. |
| 2004/0009996 A1 | 1/2004 | Moon et al. |
| 2004/0023963 A1 | 2/2004 | Cao et al. |
| 2004/0029857 A1 | 2/2004 | Hale et al. |
| 2004/0049032 A1 | 3/2004 | Charrier et al. |
| 2004/0097501 A1 | 5/2004 | Bebbington et al. |
| 2004/0097531 A1 | 5/2004 | Ledeboer et al. |
| 2004/0157893 A1 | 8/2004 | Bebbington et al. |
| 2004/0214814 A1 | 10/2004 | Bebbington et al. |
| 2004/0229875 A1 | 11/2004 | Cao et al. |
| 2005/0004110 A1 | 1/2005 | Bebbington et al. |
| 2005/0038023 A1 | 2/2005 | Bebbington et al. |
| 2005/0049246 A1 | 3/2005 | Bemis et al. |
| 2005/0228005 A1 | 10/2005 | Moon et al. |
| 2005/0234059 A1 | 10/2005 | Hale et al. |
| 2006/0270660 A1 | 11/2006 | Charrier et al. |
| 2007/0179125 A1 | 8/2007 | Fraysse |
| 2007/0190634 A1 | 8/2007 | Bebbington et al. |
| 2007/0265263 A1 | 11/2007 | Cao et al. |
| 2008/0287444 A1 | 11/2008 | Bebbington et al. |
| 2009/0181938 A1 | 7/2009 | Binch et al. |
| 2009/0221602 A1 | 9/2009 | Charrier et al. |
| 2010/0022502 A1 | 1/2010 | Jimenez et al. |
| 2010/0022507 A1 | 1/2010 | Jimenez et al. |
| 2010/0137305 A1 | 6/2010 | Binch et al. |
| 2010/0215772 A1 | 8/2010 | Mortimore et al. |
| 2010/0267628 A1 | 10/2010 | DeMattei et al. |
| 2010/0310675 A1 | 12/2010 | Binch et al. |
| 2010/0317641 A1 | 12/2010 | Mortimore et al. |
| 2011/0020376 A1 | 1/2011 | Jimenez et al. |
| 2011/0020377 A1 | 1/2011 | Pierce et al. |
| 2011/0020469 A1 | 1/2011 | Binch et al. |
| 2011/0021559 A1 | 1/2011 | Jimenez et al. |
| 2011/0046104 A1 | 2/2011 | Mortimore et al. |
| 2011/0060013 A1 | 3/2011 | Mortimore et al. |
| 2011/0086856 A1 | 4/2011 | Bebbington et al. |
| 2011/0269732 A1 | 11/2011 | Golec et al. |

FOREIGN PATENT DOCUMENTS

| | | |
|---|---|---|
| EP | 136976 | 4/1985 |
| EP | 0302312 | 2/1989 |
| GB | 2052487 | 1/1981 |
| JP | 10-130150 | 5/1998 |
| JP | 2000-026421 | 1/2000 |
| JP | 0382251 B4 | 3/2003 |
| JP | 06-65237 | 10/2007 |
| WO | 9208715 | 5/1992 |
| WO | 9322681 | 11/1993 |
| WO | 9509851 | 4/1995 |
| WO | 9515758 | 6/1995 |
| WO | 9614843 | 5/1996 |
| WO | 9709325 | 3/1997 |
| WO | 9719065 | 5/1997 |
| WO | 9802434 | 1/1998 |
| WO | 9811095 | 3/1998 |
| WO | 9814450 | 4/1998 |
| WO | 9816502 | 4/1998 |
| WO | 9838171 | 9/1998 |
| WO | 9918781 | 4/1999 |
| WO | 9941253 | 8/1999 |
| WO | 9947154 | 9/1999 |
| WO | 9962518 | 12/1999 |
| WO | 9965897 | 12/1999 |
| WO | 0012497 | 3/2000 |
| WO | 0021955 | 4/2000 |
| WO | 0039101 | 6/2000 |
| WO | 0038675 | 7/2000 |
| WO | 0042029 | 7/2000 |
| WO | 0059509 | 10/2000 |
| WO | 0078757 | 12/2000 |
| WO | 0112621 | 2/2001 |
| WO | 0139777 | 6/2001 |
| WO | 0140215 | 6/2001 |
| WO | 0144242 | 6/2001 |
| WO | 0147879 | 7/2001 |
| WO | 0147897 | 7/2001 |
| WO | 0160816 | 8/2001 |
| WO | 0164655 | 9/2001 |
| WO | 0179198 | 10/2001 |
| WO | 0174768 | 11/2001 |
| WO | 0125220 | 12/2001 |
| WO | 0208244 | 1/2002 |
| WO | 0218346 | 3/2002 |
| WO | 0222601 | 3/2002 |
| WO | 0222601 B1 | 3/2002 |

(56) References Cited

FOREIGN PATENT DOCUMENTS

| WO | 0222603 | 3/2002 |
|---|---|---|
| WO | 0224667 | 3/2002 |
| WO | 2002022602 | 3/2002 |
| WO | 0247690 | 6/2002 |
| WO | 0250065 | 6/2002 |
| WO | 0250066 | 6/2002 |
| WO | 02057259 | 7/2002 |
| WO | 02059111 | 8/2002 |
| WO | 02059112 | 8/2002 |
| WO | 02062789 | 8/2002 |
| WO | 02066461 | 8/2002 |
| WO | 02068415 | 9/2002 |
| WO | 0279197 | 10/2002 |
| WO | 03082251 | 3/2003 |
| WO | 03026664 | 4/2003 |
| WO | 03078426 | 9/2003 |
| WO | 2003077921 | 9/2003 |
| WO | 2003078427 | 9/2003 |
| WO | 03080616 | 10/2003 |
| WO | 03080616 B2 | 10/2003 |
| WO | 0400833 | 12/2003 |
| WO | 0413140 | 2/2004 |
| WO | 2004037814 | 5/2004 |
| WO | 2004072029 | 8/2004 |
| WO | 2004072029 B3 | 8/2004 |
| WO | 2007023382 | 1/2007 |
| WO | 2007041358 | 4/2007 |
| WO | 2007056163 | 5/2007 |
| WO | 2007056164 | 5/2007 |
| WO | 2007056221 | 5/2007 |
| WO | 2007059299 | 5/2007 |
| WO | 2008057940 | 5/2008 |
| WO | 2008077086 | 6/2008 |

OTHER PUBLICATIONS

Medwid, J.B. et al., "Preparation of Triazolo[ 1,5-c]pyrimidines as Potential Antiasthma Agents," J. Med. Chem. 33, 1230-1241 (1990).
Nezu, Y. et al., "Dimethoxypyrimidines as Novel Herbicides. Part 1. Synthesis and Herbicidal Activity of Dimethoxyphenoxyphenoxypyrimidines and Analogues," Pestic. Sci., 47: 103-113 (1996).
Cohen, P., "Dissection of the Protein Phosphorylation Cascades Involved in Insulin and Growth Factor Action", Biochem. Soc. Trans., 21, 555-567 (1993).
Haq, S. et al., "Glycogen Synthase Kinase-3β Is a Negative Regulator of Cardiomyocyte Hypertrophy", J. Cell Biol., 151(1), 117-129 (2000).
Fischer, P.M. et al., "Inhibitors of Cyclin-Dependent Kinases as Anti-Cancer Therapeutics", Current Med. Chem., 7, 1213-1245 (2000).
Mani, S. et al., "Cyclin-dependent kinase: novel anticancer agents", Exp. Opin. Invest. Drugs., 8, 1849-1870 (2000).
Fry, D.W. et al., "Inhibitors of cyclin-dependent kinases as therapeutic agents for the treatment of cancer", Current Opin. Oncol. Endoc. & Metab. Investig., 2-40-59 (2000).
Bokemeyer, D. et al., "Multiple intracellular MAP kinase signaling cascades", Kidney Int., 49, 1187-1198 (1996).
Anderson, N. G. et al., "Multiple intracellular MAP kinase signaling cascades", Nature, 343, 651-653 (1990).
Crews, C.M. et al., "The Primary Structure of MEK, a Protein Kinase That Phosphorylates the ERK Gene Product", Science, 258, 478-480 (1992).
Bjorbaek, C. et al, "Divergent Functional Roles for p90rsk Kinase Domains", J. Biol. Chem., 270(32), 18848-18552 (1995).
Rouse, J. et al., A Novel Kinase Cascade Triggered by Stress and Heat Shock That Stimulates MAPKAP Kinase-2 and Phosphorylation of the Small Heat Shock Proteins, Cell, 78, 1027-1037 (1994).
Raingeaud, J. et al., MMK3—and MMK6—Regulated Gene Expression Is Mediated by p38 Mitogen-Activated Protein Kinase Signal Transduction Pathway, Mol. Cell. Biol., 16, 1247-1255 (1996).
Chen, R.H. et al., "Phosphorylation of the c-Fos transrepression domain by mitogen-activated protein kinase and 90-kDa ribosomal S6 kinase", Proc. Natl. Acad. Sci. USA, 90, 10952-10956 (1993).
Moodie, S.A. et al., "Complexes of Ras-GTP with Raf-1 and Mitogen-Activated Protein Kinase Kinase", Science, 260 (5114), 1658-1661 (1993).
Frey, R.S. et al., "Involvement of Extracellular Signal-regulated Kinase 2 and Stress-activated Protein Kinase/Jun N-Terminal Kinase Activation by Transforming Growth Factor β in the Negative Growth Control of Breast Cancer Cells", Cancer Res., 57, 628-633 (1997).
Sivaraman, V.S., et al., "Hyperexpression of Mitogen-activated Protein Kinase in Human Breast Cancer", J. Clin. Invest., 99(7), 1478-1483 (1997).
Whelchel, a. et al., "Inhibition of ERK Activation Attenuates Endothelin-stimulated Airway Smooth Muscle Cell Proliferation", Am. J. Respir. Cell Mol. Biol., 16, 589-596 (1997).
Yuan, Z.Q. et al., "Frequent activation of AKT2 and induction of apoptosis by inhibition of phosphoinositide-3-OH kinase/Akt pathway in human ovarian cancer", Oncogene, 19, 2324-2330 (2000).
Kazuhiko, N. et al., "Akt/Protein Kinase B Prevents Injury-Induced Motoneuron Death and Accelerates Axonal Regeneration", J. of Neuroscience, 20(8), 2875-2986 (2000).
Molina, T.J. et al., "Profound block in thymocyte development in mice lacking p56lck", Nature, 357, 161-164 (1992).
Kimura, M. et al., "Cell Cycle-dependent Expression and Centrosome Localization of a Third Human Aurora/Ipl1—related Protein Kinase, AIK3", J. Biol. Chem., 274(11), 13766-13771 (1997).
Douglas, G. et al., "Introduction to viral diseases", Cecil Textbook of Medicine, 20th Edition, vol. 2, p. 1739-1747 (1999).
Salomon, S. et al., "Cancer Chemotherapy", Lange Medical Book, Basic and Clinical Pharmacology, 7th edition, 55, p. 881-884 (2001).
Torryiabe, K. et al., "Preparation of self-conaining arylthiazoles and insecticides", Chemical abstracts, [Columbus, Ohio, (1997).
IUPAC Compendium of Chemical Terminology on a definition of "aliphatic compounds" found from http://www.chemsoc.org/chembytes/goldbook/indexhtm (last visited on Nov. 18, 2007).
Caravajal, R. et al., "Aurora Kinases: New Targets for Cancer Therapy", Clin. Cancer Res. 2006;12(23) Dec. 1, 2006, p. 6869-6875; www.aacrjournals.org.
Gura, T. "Cancer Models: Systems for Identifying New Drugs Are Often Faulty", Science Magazine, 7 Nov. 1997, vol. 278, No. 5340, pp. 1041-1042.
Johnson, J. et al., "Relationships between drug activity in NCI preclinical in vitro and in vivo models and early clinical trials", British Journal of Cancer (2001), 84(10), pp. 1424-1431.
Gershon, H. et al., "Pyrimidines. 7. A Study of the Chlorination of Pyrimidines with Phosphorus Oxychloride in the Presence of N,N-Dimethylaniline", J. Heterocyclic Chem., 21, 1161-1167 (1984).
Ife, R.J. et al., "Reversible Inhibitors of the Gastric (H+/K+)-ATPase. 5. Substituted 2,4-Diaminoquinazolines and Thienopyrimidines", J. Med. Chem., 38(14); 2763-2773 (1995).
Tanji, K. et al., "Purines. X. Reactivities of Methyl Groups on 9-Phenylpurines : Condensation with an Aldehyde or an Ester, and Oxidation with Selenium Dioxide", Chem. Phar. Bull., 40 (1), 227-229 (1992).
Charpiot, B. et al., "Quinazolines: Combined type 3 and 4 phosphodiesterase inhibitors", Bioorg. Med. Chem. Lett., 8 (20), 2891-2896 (1998).
Shikhaliev, K.S. et al., "Heterocyclization of quinazol-2-ylguanidines. 1. Reaction with amino acids", Chem. Heterocycl. Compd., 35 (7), 818-820 (1999).
Singh, S.P. et al., "Synthesis & Mass Spectra of Some Substituted 2-(2'-Benzazolylamino)pyrimidines", Indian J. Chem. Sect. B, 22(1); 37-42 (1983).
Ti, J. et al., "Anticandidal activity of pyrimidine-peptide conjugates", J. Med. Chem., 23(8), 913-918 (1980).
Kretzschmar, E. et al., "Synthese von 2,6-disubstituierten 4-Hydroxy-5,6,7,8-tetrahydropyrido[4,3-d]pyrimidinen", Pharmazie, 43(7), 475-476 (1988).
Norman, M.H. et al., "Structure-Activity Relationships of a Series of Pyrrolo[3,2-d]pyrimidine Derivatives and Related Compounds as Neuropeptide Y5 Receptor Antagonists", J. Med. Chem., 43(22), 4288-4312 (2000).

(56) References Cited

OTHER PUBLICATIONS

Nugent, R.A. et al., "Pyrimidine Thioethers: A Novel Class of HIV-1 Reverse Transcriptase Inhibitors with Activity Against Bhap-Resistant HIV", J. Med. Chem., 41, 3793-3803 (1998).
Myers, M.R. et al., "The synthesis and SAR of new 4-(N-alkyl-N-phenyl)amino-6,7-dimethoxyquinazolines and 4-(Nalkyl-N-phenyl)aminopyrazolo[3,4-d]pyrimidines, inhibitors of CSF-1R tyrosine kinase activity", Bioorg. Med. Chem. Lett, 7, 4, 421-424 (1997).
Agarwal, N. et al., "Suitably functionalised pyrimidines as potential antimycotic agents", Bioorg. Med. Chem. Lett., 10, 8, 703-706 (2000).
Crespo, M.I. et al., "Design, Synthesis, and Biological Activities of New Thieno[3,2-d]pyrimidines as Selective Type 4 Phosphodiesterase Inhibitors", J. Med. Chem., 41 (21), 4021-4035 (1998).
Noell, C.W. et al., "Potential Purine Antagonists. XX. The Preparation and Reactions of Some Methylthiopurines", J. Am. Chem. Soc., 81(22), 5997-6007 (1959).
Lubbers, T. et al., "Design, synthesis, and structure—activity relationship studies of ATP analogues as DNA gyrase inhibitors", Bioorg. Med. Chem. Lett., 10, 8, 821-826 (2000).
D'Atri, G. et al., "Novel pyrimidine and 1,3,5-triazine hypolipemic agents", J. Med. Chem. 27(12), 1621-1629 (1984).
Venugopalan, B. et al., "Synthesis and antimalarial activity of pyrido[3,2-f)quinozalines and their oxides", Indian J. Chem. Sect. B, 34, 9, 778-790 (1995).
Curd, F.H.S. et al, "Synthetic antimalarials. Part XVII. Some aminoalkylaminoquinoline derivatives", J. Chem. Soc., 899-909 (1947).
Haworth, R.D. et al., "Synthetic antimalarials. Part XXVII. Some derivatives of phthalazine, quinoxaline, and isoquinoline", J. Chem. Soc., 777-782 (1948).
Nair, M.D., et al., "3-Chloroisocarbostyril & Its Chlorination Products", Indian J. Chem., 467-470 (1967).
Jeffery, J.E. et al., "Synthesis of sibutramine, a novel cyclobutylalkylamine useful in the treatment of obesity, and its major human metabolites", J. Chem. Soc., Perkin Trans. 1, 21, 2583-2589 (1996).
Gnecco, D. et al., "An Improved Preparation of 1-Methyl-4-Cyano-4-phenylpiperidine", Org. Prep. Proced. Int., 18 (4), 478-480 (1996).
Fedorynski, M. et al., "Synthesis of 1-Arycyclopropanecarbonitriles under Phase-transfer Catalytic Conditions", Org. Prep. Proced. Int., 27(3), 355-359 (1995).
Suzuki, S. et al., "Application of electrogenerated triphenylmethyl anion as a base for alkylation of arylacetic esters and arylacetonitriles and isomerization of allylbenzenes", Can. J. Chem., 72(2): 357-361 (1994).
Prasad, G. et al., "18-Crown-6 as a catalyst in the dialkylation of o-nitrophenacyl derivatives", J. Org. Chem., 25, 7188-7190 (1991).
Moss, R.A. et al., "Conversion of 'Obstinate' Nitriles to Amidines by Garigipati's Reaction", Tetrahedron Lett., 36(48), 8761-8764 (1995).
Garigipati, R.S., "An efficient conversion of nitriles to amidines", Tetrahedron Lett., 31(14), 1969-1972 (1990).
Warner, S.L. et al, "Targeting Aurora-2 Kinase in Cancer," Mol. Cancer Thera., 2, 589-585, 2003.
Wagman, A.S. et all, "Discovery and Development of GSK3 Inhibitors for the Treatment of Type 2 Diabetes," Current Pharmaceutical Design, 10, 1105-1137 (2004).
Nezu, Y. et al., "Dimethoxypyrimidines as Novel Herbicides. Part 2. Synthesis and Herbicidal Activity of Dimethoxyphenoxyphenoxypyrimidines and Analogues," Pestic. Sci., 47: 115-124 (1996).
Tanaka, T.U. et al., "Evidence that the Ipl1-Sli15 (Aurora Kinase-INCENP) Complex Promotes Chromosome Bi-orientation by Altering Kinetochore-Spindle Pole Connections," Cell, 108, 317-329 (2002).
Soriano, P. et al., "Targeted Disruption of the C-SIC Pmto-Oncogene Leads to Osteopetrosis in Mice," Cell, 64: 693-702, (1991).

Campbell, S.F. et al., "2,4-Diamino-6,7-dimethoxyquinazolines. 3.2-(4-Heterocyclylpiperazin-l-yl) Derivatives as α1-Adrenoceptor Antagonists and Antihypertensive Agents," J. Med. Chem., 30, 1794-1798 (1987).
Casanova, B. et al., "Revisión critica de la patogenia actual de la esclerosis multiple y futuras direcciones posibles," Rev. Neurol., 28 (9): 909-915 (1999).
Cline, G.W. et al., "Effects of a Novel Glycogen Synthase Kinase-3 Inhibitor on Insulin-Stimulated Glucose Metabolism in Zucker Diabetic Fatty (fa/fa) Rats," Diabetes, 51, 2903-2910 (2002).
Simone, J.V., "Oncology: Introduction" in Cecil Textbook in Medicine, 20th ed., vol. 1, 1004-1010 (1996).
Coleman, R.A., "The Biological Evaluation of New Compounds" in Medicinal Chemistry: Principles and Practice, King, Frank D. ed, Royal Society of Chemistry, 53-66 (1994).
The Condensed Chemical Dictionary, Sixth Edition by Arthur and Elizabeth Rose, 38 (1961).
Damasio, A.R., "Alzheimer's Disease and Related Dementia," in Cecil Textbook of Medicine, 20th ed., 2: 1992-1996 (1996).
Rogers, E. et al., "The aurora kinase AIR-2 functions in the release of chromosome cohesion in Caenorhabditis elegans meiosis," J. Cell Biol., 157(2): 219-229 (2002).
Fisher A., "Therapeutic Strategies in Alzheimer's Disease: M1 Muscarinic Agonists," Jpn. J. Pharmacol., 84(2):101-12 (2000).
Frame, M.C., "Src in cancer: deregulation and consequences for cell behaviour," Biochimica et Biophysica Acta., 1602, 114-130 (2002).
Frampton, J.E. et al., "Pentoxifylline (Oxpentifylline)—A Review of its Therapeutic Efficacy in the Management of Peripheral Vascular and Cerebrovascular Disorder," Drugs & Aging, 7(6): 480-503 (1995).
Ganellin, C.R., "Past Approaches to Discovering New Drugs as Medicines" in Medicinal Chemistry, Principles and Practices. King, Frank D. ed, Royal Society of Chemistry, 189-205 (1994).
Hamdane, M. et al., "A Therapeutic Target in Alzheimer Neurodegeneration," J. Mol. Neurosci., 19(3): 275-87 (2002).
Hardt, S.E. et al., "Glycogen Synthase Kinase-3β—A Novel Regulator of Cardiac Hypertrophy and Development," Circulation Research, 90: 1055-1063 (2002).
Parnell, E.W., "2-Cyano-4-nitrophenylhydrazine and 3-Amino-5-nitroindazole", J. Chem. Soc., 2363-2365 (1959).
Heaney, F. et al., "Pyrimidine annelated heterocycles—synthesis and cycloaddition of the first pyrimido[1,4]diazepine N-oxides," J. Chem. Soc., Perkin Trans. 1, 622-632 (2001).
Henriksen, E.J. et al., "Modulation of muscle insulin resistance by selective inhibition of GSK-3 in Zucker diabetic fatty rats," Am. J. Physiol. Endocrinol. Metab., 284: E892-E900 (2003).
Okafor, C.O., "Studies in the Heterocyclic Series. X. 1,3,9-Triazaphenothiazine Ring System, a New Phenothiazine Ring," J. Org. Chem., 40(19): 2753-2755 (1975).
Namikowa et al., "Akt/Protein Kinase B Prevents Injury-Induced Motoneuron Death and Accelerates Axonal Regeneration", The Journal of Neuroscience, Apr. 15, 2000, 20(8):2875-2886.
Alonso, M. et al., "GSK-3 Inhibitors: Discoveries and Developments", Current Medicinal Chemistry, 11, 755-763 (2004).
Anonymous, "Vertex Inhbitors of Aurora-2, glycogen synthase kinase-3 and Src Kinase", Expert Opin. Ther. Patents, 14(3): 439-443 (2004).
Baig, G.U. et al., "Triazines and Related Products. Part 28' Conversion of 3-Aryl-I-(2-cyanophenyl) triazenes into 3-Arylqu i nazol i n-4(3H) -ones with Formamide" J. Chem. Soc. Perkin Trans. I, 3765-2766 (1984).
Bischoff, J.R., et al., "A homologue of Drosophila aurora kinase is oncogenic and amplified in human colorectal cancers", The EMBO Journal, 17(11): 3052-3065 (1998).
Bischoff, J.R., et al., "The Aurora/Ipl1p kinase family: regulators of chromosome segregation and cytokinesis", Cell Biology, 9, 454-459 (1999).
Brunswick, D.J. et al., "Cyclic Amidines. Part XXII. Novel Isomerism of Disubstituted Tricyclooquinazolines and Molecular Orientations in Carcinogenesis", J. Chem. Soc. (C), 2641-2647 (1970).
Wolff, M.E., "Burger's Medicinal Chemistry and Drug Discovery," 5th ed., vol. 1: Principles and Practice, 975-977 (1995).

(56) References Cited

OTHER PUBLICATIONS

Cohen, P. et al., "The renaissance of GSK3," Nat. Rev. Mol. Biol., 2, 769-776 (2001).

Eldar-Finkelman, H. et al., "Challenges and opportunities with glycogen synthase kinase-3 inhibitors for insulin resistance and Type 2 diabetes treatment," Expert Opinion on Investigational Drugs, 12(9): 1511-1519 (2003).

Harrington, E.A. et al., "VX-680, a potent and selective small-molecule inhibitor of the Aurora kinases, suppresses tumor growth in vivo," Nat. Med., 10(3): 262-267 (2004).

Heutink, P., "Untangling tau-related dementia", Hum. Mol. Genet., 9(6): 979-986 (2000).

Nigg, E.A., "Mitotic Kinases as Regulators of Cell Division and its Checkpoints," Nat. Rev. Mol. Cell Biol., 2: 21-32 (2001).

Traxler, P. et al., "Use of a Pharmacophore Model for the Design of EGF-R Tyrosine Kinase Inhibitors: 4-(Phenylamino)pyrazolo[3,4-d]pyrimidines," J. Med. Chem., 40, 3601-3616 (1997).

Nakajima, Y. et al., "Pyrazoles agricultural and horticultural bactericides," CAPLUS listing Accession No. 1994:292136, JP 06065237 (1994).

Kelarev, V.I. et al., "Synthesis of amino derivatives of 1,3,5-triazine containing 1,3-4-thiadiazole fragments," DATABASECA "Online!" Chemical Abstract Service, Columbus, OH, US; Database Accession No. 1998:69514 XP002242653 abstract & Izvestiya Vysshikh Uchebnkh Zavedenii, Khimiya I Khimicheskaya Tekhnologiya, 40(5): 27-32 (1997).

Chalmers, D.T. et al., "Corticotrophin-releasing factor receptors: from molecular biology to drug design," TiPS, 17, 769-776 (2001).

Kim, L. et al., "GSK3, a master switch regulating cell-fate specification and tumorigenesis," Current Opinion in Genetics & Development, 10:508-514 (2000).

Lyrer, P., Schweiz. Med. Woohen Schr., 124(45); 2005-2012 (1994).

Banker, G.S. et al., "Modern Pharmaceutics", 451 & 596, 3rd ed., Marcel Dekker, New York (1996).

Lovestone, S. et al., "Alzheimer's disease-like phosphorylation of the microtubule-associated protein tau by glycogen synthase kinase-3 in transfected mammalian cells", Curr. Biol., 4(12), 1077-86 (1994).

Ivashchenko A. V. et al., "Synethsis and Study of Heteroaromatic Ligands Containing a Pyrimidine Ring", Khim. Geterotsikl. Soedin., (12), 1673-7, (1980) (in English).

Brownlees, J. et al., "Tau phosphorylation in transgenic mice expressing glycogen synthase kinase-3beta transgenes", Neuroreport., 8(15), 3251-5 (1997).

Biagi, G. et al., "Synthesis of 4,6 Disubstituted and 4,5,6-Trisubstituted-2-Phenyl-pyrimidines and Their Affinity Towards Al Adenosine Receptors", Farmaco., 52(1), 61-65 (1997).

Ali, N.M. et al, "Palladium-Catalyzed Cross Coupling Reactions of Arylboronic Acids with Pi-Deficient Heteroaryl Chlorides" Tetrahedron, 48 (37), 8117-8126 (1992).

Zhang, Z. et al., "Destabilization of β catenin by mutations in presenilin-1 potentiates neuronal apoptosis", Nature, 395, 698-702 (1998).

Takashima, K. et al., "Tau Protein Kinase I is Essential for Amyloid β-Protein-Induced Neurotoxicity", PNAS 90, 7789-7793 (1993).

Pei, J. et al., "Distribution, Levels, and Activity of Glycogen Synthase Kinase-3 in the Alzheimer Disease Brain", J. Neuropathol. Exp., 56, 70-78 (1997).

Rueeger, H et al., "Design, synthesis and SAR of a series of 2-substituted 4-amino-quinazoline neuropeptide Y Y5 receptor antagonists", Bioorg. Med. Chem. Lett., 10(11), 1175-1180 (2000).

Glossary of Class Names of Organic Compounds and Reactive Intermediates Based on Structure found from http://www.chem.qmul.ac.uk/iupac/class/index.html (last visited on Nov. 18, 2007).

Nomenclature found from http://www.cem.msu.edu/~reusch/VirtualText/nomen1.htm (last visited on Nov. 18, 2007).

Coghlan, M.P. et al., "Selective small molecule inhibitors of glycogen synthase kinase-3 modulate glycogen metabolism and gene transcription", Chemistry & Biology, 7, 793-83 (2000).

Klein, P.S. et al., "A molecular mechanism for the effect of lithium on development", PNAS, 93: 8455-8459 (1996).

Cross, D.A.E. et al., The inhibition of glycogen synthase kinase-3 by insulin or insulin-like growth factor 1 in the rat skeletal muscle cell line L6 is blocked by wortmannin, but not by rapamycin: evidence that wortmannin blocks activation of the mitogen-activated protein kinase pathway in L6 cells between Ras and Raf', Biochem J., 303: 21-26 (1994).

Massillon, D. et al., "Identification of the glycogenic compound 5-iodotubercidin as a general protein kinase inhibitor", Biochem J., 299: 123-128 (1994).

Fox T. et al. "A single amino acid substitution makes ERK2 susceptible to pyridinyl imidazole inhibitors of p38 MAP kinase", Protein Sci., 7:2249-2255 (1998).

Takayanagi, H. et al., "Suppression of arthritic bone destruction by adenovirus-mediated csk gene transfer to synoviocytes and osteoclasts", J. Clin. Invest., 104, 137-146 (1999).

Boschelli et al., "Small molecule inhibitors of Src family kinases", Drugs of the Future, 25(7): 717-736 (2000).

Talamonti, M.S. et al., "Increase in activity and level of pp60c-src in progressive stages of human colorectal cancer", J Clin Invest., 91(1): 53-60 (1993).

Lutz M.L. et al., "Overexpression and Activation of the Tyrosine Kinase Src in Human Pancreatic Carcimona", Biochem. Biophys. Res. 243, 503-508 (1998).

Rosen, N. et al., "Analysis of pp60c-src Protein Kinase Activity in Human Tumor Cell Lines and Tissues", J.Biol. Chem., 261, 13754-13759 (1986).

Bolen, J.B. et al., "Activation of pp60c-src protein kinase activity in human colon carcinoma", PNAS, 84, 2251-2255 (1987).

Masaki, T. et al., "pp60c-src Activation in Hepatocellular Carcinoma of Humans and LEC Rats", Hapatology, 27, 1257 (1998).

Biscardi, J.S. et al., "c-Src, Receptor Tyrosine Kinases, and Human Cancer", Adv. Cancer Res., 76, 61 (1999).

Lynch, S.A. et al., "Increased Expression of the src Proto-Oncogene in Hairy Cell Leukemia and a Subgroup of B-Cell Lymphomas", Leukemia, 7(9), 1416-1422 (1993).

Wiener, J.R., "Decreased Src Tyrosine Kinase Activity Inhibits Malignant Human Ovarian Cancer Tumor Growth in a Nude Mouse Model", Clin. Cancer Res., 5, 2164-2170 (1999).

Staley, C.A. et al., "Decreased Tumorigenicity of a Human Colon Adenocarcinoma Cell Line by an Antisense Expression Vector Specific for c-Src", Cell Growth Diff., 8, 269-274 (1997).

Singhal, N. et al., "Synthesis and Antimalarial Activity of Some New Quinazoline Derivatives", Indian Chem. Soc., 61, 690-693 (1984).

Kim, Y.Z. et al., "Synthesis and Antimicrobial Activity of Novel [(3-Aminopyrimidiniumyl)thio]methyl Cephalosporins", J. Med. Chem., 37(22); 3828-3833 (1994).

Patel et al., "Synthesis and Biological Activity of Substituted 1,4,5,6-tetrahydropyridazin-4-ones, 5,6-dihydro-3-hydroxy-1H-pyrazolo[4,3-c]pyridazines and 2,8-dihydro-1H-pyrano [2,3-d]pyridazines", Indian Journal of Chemistry, vol. 28B, pp. 733-744, Sep. 1989.

Ghozlan et al. "Synthesis of Polyfuncionally Substituted Pyridazines", Liebigs. Ann. Chem., pp. 293-296, 1990.

Ghozlan et al. "Reactions with 3-oxo-2-phenylhydrazonobutyronitrile: New Routes for the Synthesis of Pyradizines", Gazzetta Chimica Italiana, vol. 119, pp. 95-97, 1989.

Witherington et al. "5-Aryl-pyrazolo[3-4-b]pyridazines: Potent Inhibitors of Glycogen Synthase Kinase-3 (GSK-3)", Bioorganic & Medical Chemistry Letters, vol. 13, pp. 1581-1584, 2003.

International Search Report received in the corresponding PCT Application No. PCT/US2004/003061, (Oct. 21, 2004).

\* cited by examiner

COMPOSITIONS USEFUL AS INHIBITORS OF PROTEIN KINASES

CROSS REFERENCE TO RELATED APPLICATIONS

This application is a divisional of U.S. patent application Ser. No. 10/772,219, filed Feb. 4, 2004; which claims the benefit, under 35 U.S.C. §119 to U.S. Provisional Application No. 60/445,529, filed Feb. 6, 2003, entitled "Compositions Useful as Inhibitors of Protein Kinases," the entire contents of which are hereby incorporated by reference.

TECHNICAL FIELD OF THE INVENTION

The present invention relates to compounds useful as inhibitors of protein kinases. The invention also provides pharmaceutically acceptable compositions comprising the compounds of the invention and methods of using the compositions in the treatment of various disorders.

BACKGROUND OF THE INVENTION

The search for new therapeutic agents has been greatly aided in recent years by a better understanding of the structure of enzymes and other biomolecules associated with target diseases. One important class of enzymes that has been the subject of extensive study is protein kinases.

Protein kinases mediate intracellular signal transduction. They do this by effecting a phosphoryl transfer from a nucleoside triphosphate to a protein acceptor that is involved in a signaling pathway. There are a number of kinases and pathways through which extracellular and other stimuli cause a variety of cellular responses to occur inside the cell. Examples of such stimuli include environmental and chemical stress signals (e.g., osmotic shock, heat shock, ultraviolet radiation, bacterial endotoxin, and H2O2), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis and regulation of cell cycle.

Many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies and asthma, Alzheimer's disease and hormone-related diseases. Accordingly, there has been a substantial effort in medicinal chemistry to find protein kinase inhibitors that are effective as therapeutic agents.

Glycogen synthase kinase-3 (GSK-3) is a serine/threonine protein kinase comprised of α and β isoforms that are each encoded by distinct genes [Coghlan et al., *Chemistry & Biology*, 7, 793-803 (2000); Kim and Kimmel, *Curr. Opinion Genetics Dev.*, 10, 508-514 (2000)]. GSK-3 has been implicated in various diseases including diabetes, Alzheimer's disease, CNS disorders such as manic depressive disorder and neurodegenerative diseases, and cardiomyocyte hypertrophy [see, e.g., WO 99/65897; WO 00/38675; Kaytor and Orr, *Curr. Opin. Neurobiol.*, 12, 275-8 (2000); Haq et al., *J. Cell Biol.*, 151, 117-30 (2000); Eldar-Finkelman, *Trends Mol. Med.*, 8, 126-32 (2002)]. These diseases are associated with the abnormal operation of certain cell signaling pathways in which GSK-3 plays a role.

GSK-3 has been found to phosphorylate and modulate the activity of a number of regulatory proteins. These include glycogen synthase, which is the rate-limiting enzyme required for glycogen synthesis, the microtubule-associated protein Tau, the gene transcription factor β-catenin, the translation initiation factor e1F-2B, as well as ATP citrate lyase, axin, heat shock factor-1, c-Jun, c-myc, c-myb, CREB, and CEPBα. These diverse targets implicate GSK-3 in many aspects of cellular metabolism, proliferation, differentiation and development.

In a GSK-3 mediated pathway that is relevant for the treatment of type II diabetes, insulin-induced signaling leads to cellular glucose uptake and glycogen synthesis. GSK-3 is a negative regulator of the insulin-induced signal in this pathway. Normally, the presence of insulin causes inhibition of GSK-3-mediated phosphorylation and deactivation of glycogen synthase. The inhibition of GSK-3 leads to increased glycogen synthesis and glucose uptake [Klein et al., *PNAS*, 93, 8455-9 (1996); Cross et al., *Biochem. J.*, 303, 21-26 (1994); Cohen, *Biochem. Soc. Trans.*, 21, 555-567 (1993); and Massillon et al., *Biochem J.* 299, 123-128 (1994); Cohen and Frame, *Nat. Rev. Mol. Cell. Biol.*, 2, 769-76 (2001)]. However, where the insulin response is impaired in a diabetic patient, glycogen synthesis and glucose uptake fail to increase despite the presence of relatively high blood levels of insulin. This leads to abnormally high blood levels of glucose with acute and chronic effects that may ultimately result in cardiovascular disease, renal failure and blindness. In such patients, the normal insulin-induced inhibition of GSK-3 fails to occur. It has also been reported that GSK-3 is overexpressed in patients with type II diabetes [WO 00/38675]. Therapeutic inhibitors of GSK-3 are therefore useful for treating diabetic patients suffering from an impaired response to insulin.

Apoptosis has been implicated in the pathophysiology of ischemic brain damage (Li et al., 1997; Choi, et al., 1996; Charriaut-Marlangue et al., 1998; Grahm and Chen, 2001; Murphy et al., 1999; Nicotera et al., 1999). Recent publications indicate that activation of GSK-3β may be involved in apoptotic mechanisms (Kaytor and Orr, 2002; Culbert et al., 2001). Studies in rat models of ischemic stroke induced by middle cerebral artery occlusion (MCAO) showed increased GSK-3β expression is following ischemia (Wang et al., *Brain Res.*, 859, 381-5 (2000); Sasaki et al., *Neurol Res.*, 23, 588-92 (2001)). Fibroblast growth factor (FGF) reduced ischemic brain injury after permanent middle cerebral artery occlusion (MCO) in rats (Fisher et al. 1995; Song et al. 2002). Indeed, the neuroprotective effects of FGF demonstrated in ischemia models in rats may be mediated by a PI-3 kinase/AKT-dependent inactivation of GSK-3β (Hashimoto et al., 2002). Thus, inhibition of GSK-3β after a cerebral ischemic event may ameliorate ischemic brain damage.

GSK-3 is also implicated in mycardial infarction. See Jonassen et al., *Circ Res.*, 89, 1191 (2001) (The reduction in myocardial infarction by insulin administration at reperfusion is mediated via Akt dependent signaling pathway.); Matsui et al., *Circulation*, 104, 330 (2001) (Akt activation preserves cardiac function and prevents cardiomyocyte injury after transient cardiac ischemia in vivo); Miao et al., *J. Mol. Cell. Cardiol.*, 32, 2397 (2000) (Intracoronary, adenovirus-mediated Akt gene delivery in heart reduced gross infarct size following ischemia-reperfusion injury in vivo); and Fujio et al., *Circulation*, 101, 660 (2000) (Akt signaling inhibits cardiac myocyte apoptosis in vitro and protects against ischemia-reperfusion injury in mouse heart).

GSK-3 activity plays a role in head trauma. See Noshita et al., *Neurobiol. Dis.*, 9, 294 (2002) (Upregulation of Akt/PI3-kinase pathway may be crucial for cell survival after traumatic brain injury) and Dietrich et al., *J. Neurotrauma*, 13, 309 (1996) (Posttraumatic administration of bFGF significantly reduced damaged cortical neurons & total contusion volume in a rat model of traumatic brain injury).

GSK-3 is also known to play a role in psychiatric disorders. See Eldar-Finkelman, *Trends Mol. Med.*, 8, 126 (2002); Li et al., *Bipolar Disord.*, 4, 137 (2002) (LiCl and Valproic acid, anti-psychotic, mood stabilizing drugs, decrease GSK-3 activities and increase beta-catenin) and Lijam et al., *Cell*, 90, 895 (1997) (Dishevelled KO mice showed abnormal social behavior and defective sensorimotor gating. Dishevelled, a cytoplamic protein involved in WNT pathway, inhibits GSK-3beta activities).

It has been shown that GSK-3 inhibition by lithium and valproic acid induces axonal remodeling and change synaptic connectivity. See Kaytor & Orr, *Curr. Opin. Neurobiol.*, 12, 275 (2002) (Downregulation of GSK-3 causes changes in microtubule-associated proteins: tau, MAP1 & 2) and Hall et al., *Mol. Cell. Neurosci.*, 20, 257 (2002) (Lithium and valproic acid induces the formation of growth cone-like structures along the axons).

GSK-3 activity is also associated with Alzheimer's disease. This disease is characterized by the presence of the well-known β-amyloid peptide and the formation of intracellular neurofibrillary tangles. The neurofibrillary tangles contain hyperphosphorylated Tau protein, in which Tau is phosphorylated on abnormal sites. GSK-3 has been shown to phosphorylate these abnormal sites in cell and animal models. Furthermore, inhibition of GSK-3 has been shown to prevent hyperphosphorylation of Tau in cells [Lovestone et al., *Curr. Biol.*, 4, 1077-86 (1994); and Brownlees et al., *Neuroreport*, 8, 3251-55 (1997); Kaytor and Orr, *Curr. Opin. Neurobiol.*, 12, 275-8 (2000)]. In transgenic mice overexpressing GSK-3, a significant increase in Tau hyperphosphorylation and abnormal morphology of neurons was observed [Lucas et al., *EMBO J.*, 20, 27-39 (2001)]. Active GSK-3 accumulates in cytoplasm of pretangled neurons, which can lead to neurofibrillary tangles in brains of patients with AD [Pei et al., *J. Neuropathol. Exp. Neurol.*, 58, 1010-19 (1999)]. Therefore, inhibition of GSK-3 slows or halts the generation of neurofibrillary tangles and thus can treat or reduce the severity of Alzheimer's disease.

Evidence for the role GSK-3 plays in Alzheimer's disease has been shown in vitro. See Aplin et al., *J. Neurochem.* 67, 699 (1996); Sun et al., *Neurosci. Lett.* 321, 61 (2002) (GSK-3b phosphorylates cytoplasmic domain of Amyloid Precursor Protein (APP) and GSK-3b inhibition reduces Ab40 & Ab42 secretion in APP-transfected cells); Takashima et al., *PNAS*, 95, 9637 (1998); Kirschenbaum et al. (2001), *J. Biol. Chem.*, 276, 7366 (2001) (GSK-3b complexes with and phosphorylates presenilin-1, which is associated with gamma-secretase activity in the synthesis of Aβ from APP); Takashima et al., (1998), *Neurosci. Res.* 31, 317 (1998) (Activation of GSK-3b by Ab(25-35) enhances phosphorylation of tau in hippocampal neurons. This observation provides a link between Aβ and neurofibrillary tangles composed of hyperphosphorylated tau, another pathological hallmark of AD); Takashima et al., *PNAS*, 90, 7789 (1993) (Blockade of GSK-3b expression or activity prevents Ab-induced neuro-degeneration of cortical and hippocampal primary cultures); Suhara et al., *Neurobiol. Aging*, 24, 437 (2003) (Intracellular Ab42 is toxic to endothelial cells by interfering with activation of the Akt/GSK-3b signaling-dependent mechanism); De Ferrari et al., *Mol. Psychiatry*, 8, 195 (2003) (Lithium protects N2A cells & primary hippocampal neurons from Aβ fibril-induced cytotoxicity, & reduces nuclear translocation/destabilization of b-catenin); and Pigino et al., *J. Neurosci.*, 23, 4499 (2003) (The mutations in Alzheimer's presenilin 1 may deregulate and increase GSK-3 activity, which in turn, impairs axonal transport in neurons. The consequent reductions in axonal transport in affected neurons can ultimately lead to neurodegeneration).

Evidence for the role GSK-3 plays in Alzheimer's disease has been shown in vivo. See Yamaguchi et al., (1996), *Acta Neuropathol.*, 92, 232 (1996); Pei et al., *J. Neuropath. Exp. Neurol.* 58, 1010 (1999) (GSK-3b immunoreactivity is elevated in susceptible regions of AD brains); Hernandez et al., *J. Neurochem.*, 83, 1529 (2002) (Transgenic mice with conditional GSK-3b overexpression exhibit cognitive deficits similar to those in transgenic APP mouse models of AD); De Ferrari et al., *Mol. Psychiatry*, 8, 195 (2003) (Chronic lithium treatment rescued neurodegeneration and behavioral impairments (Morris water maze) caused by intrahippocampal injection of Aβ fibrils.); McLaurin et al., *Nature Med.*, 8, 1263 (2002) (Immunization with Aβ in a transgenic model of AD reduces both AD-like neuropathology and the spatial memory impairments); and Phiel et al., *Nature*, 423, 435 (2003) (GSK-3 regulates amyloid-beta peptide production via direct inhibition of gamma secretase in AD tg mice).

Presenilin-1 and kinesin-1 are also substrates for GSK-3 and relate to another mechanism for the role GSK-3 plays in Alzheimer's disease, as was recently described by Pigino, G., et al., *Journal of Neuroscience*, 23, 4499 (2003). It was found that GSK-3beta phosphorylates kinsesin-I light chain, which results in a release of kinesin-1 from membrane-bound organelles, leading to a reduction in fast anterograde axonal transport (Morfini et al., 2002). The authors suggest that the mutations in PSI may deregulate and increase GSK-3 activity, which in turn, impairs axonal transport in neurons. The consequent reductions in axonal transport in affected neurons ultimately leads to neurodegeneration.

GSK-3 is also associated with amyotrophic lateral sclerosis (ALS). See Williamson and Cleveland, 1999 (Axonal transport is retarded in a very early phase of ALS in mSOD1 mice); Morfini et al., 2002 (GSK3 phosphorylates kinesin light chains and inhibit anterograde axonal transport); Warita et al., *Apoptosis*, 6, 345 (2001) (The majority of spinal motor neurons lost the immunoreactivities for both PI3-K and Akt in the early and presymptomatic stage that preceded significant loss of the neurons in this SOD1 tg animal model of ALS); and Sanchez et al., 2001 (The inhibition of PI-3K induces neurite retraction mediated by GSK-3 activation).

GSK-3 activity is also linked to spinal cord and peripheral nerve injuries. It has been shown that GSK-3 inhibition by lithium and valproic acid can induce axonal remodeling and change synaptic connectivity. See Kaytor & Orr, *Curr. Opin. Neurobiol.*, 12, 275 (2002) (Downregulation of GSK-3 causes changes in microtubule-associated proteins: tau, MAP1 & 2) and Hall et al., *Mol. Cell. Neurosci.*, 20, 257 (2002) (Lithium and valproic acid induces the formation of growth cone-like structures along the axons). See also Grothe et al., *Brain Res.*, 885, 172 (2000) (FGF-2 stimulates Schwann cell proliferation and inhibits myelination during axonal growth); Grothe and Nikkhah, 2001 (FGF-2 is up regulated in the proximal and distal nerve stumps within 5 hours after nerve crush); and Sanchez et al., 2001 (The inhibition of PI-3K induces neurite retraction mediated by GSK-3 activation).

Another substrate of GSK-3 is β-catenin, which is degraded after phosphorylation by GSK-3. Reduced levels of β-catenin have been reported in schizophrenic patients and have also been associated with other diseases related to increase in neuronal cell death [Zhong et al., *Nature*, 395, 698-702 (1998); Takashima et al., *PNAS*, 90, 7789-93 (1993); Pei et al., *J. Neuropathol. Exp.*, 56, 70-78 (1997); and Smith et al., *Bioorg. Med. Chem.* 11, 635-639 (2001)]. Furthermore, β-catenin and Tcf-4 play a dual role in vascular remodeling by inhibiting vascular smooth muscle cell apoptosis and promoting proliferation (Wang et al., *Circ. Res.*, 90, 340 (2002). Accordingly, GSK-3 is associated with angiogenic disorders. See also Liu et al., *FASEB J.* 16, 950 (2002) (Activation of GSK-3 reduces hepatocyte growth factor, leading to altered endothelial cell barrier function and diminished vascular integrity.) and Kim et al., *J. Biol. Chem.*, 277, 41888 (2002) (GSK-3beta activation inhibits angiogenesis in vivo using a Matrigel plug assay: the inhibition of GSK-3beta signalling enhances capillary formation).

Association between GSK-3 and Huntington's disease has been shown. See Carmichael et al., *J. Biol. Chem.*, 277, 33791 (2002) (GSK-3beta inhibition protect cells from polyglutamine-induced neuronal and non-neuronal cell death via increases in b-catenin and its associated transcriptional pathway). Overexpression of GSK-3 reduced the activation of heat shock transcription factor-1 and heat shock protein HSP70 (Bijur et al., *J. Biol. Chem.*, 275, 7583 (2000) that are shown to decrease both poly-(Q) aggregates and cell death in in vitro HD model (Wyttenbach et al., *Hum. Mol. Genet.*, 11, 1137 (2002)).

GSK-3 effects the levels of FGF-2 and their receptors which are increased during remyelination of brain aggregate cultures in remyelinating rat brains. See Copelman et al., 2000, Messersmith, et al., 2000; and Hinks and Franklin, 2000. It was also found that FGF-2 induces process outgrowth by oligodendrocytes implicating involvement of FGF in remyelination (Oh and Yong, 1996; Gogate et al., 1994) and that FGF-2 gene therapy has shown to improve the recovery of experimental allergic encephalomyelitis (EAE) mice (Ruffini, et al., 2001).

GSK-3 has also been associated with hair growth because Wnt/beta-catenin signaling is shown to play a major role in hair follicle morphogenesis and differentiation (Kishimotot et al., *Genes Dev.*, 14, 1181 (2000); Millar, *J. Invest. Dermatol.*, 118, 216 (2002)). It was found that mice with constituitive overexpression of the inhibitors of Wnt signaling in skin failed to develop hair follicles. Wnt signals are required for the initial development of hair follicles and GSK-3 constituitively regulates Wnt pathways by inhibiting beta-catenin. (Andl et al., *Dev. Cell*, 2, 643 (2002)). A transient Wnt signal provides the crucial initial stimulus for the start of a new hair growth cycle, by activating beta-catenin and TCF-regulated gene transcription in epithelial hair follicle precursors (Van Mater et al., *Genes Dev.*, 17, 1219 (2003)).

Because GSK-3 activity is associated with sperm motility, GSK-3 inhibition is useful as a male contraceptive. It was shown that a decline in sperm GSK-3 activity is associated with sperm motility development in bovine and monkey epididymis. (Vijayaraghavan et al., *Biol. Reprod.*, 54, 709 (1996); Smith et al., *J. Androl.*, 20, 47 (1999)). Furthermore, tyrosine & serine/threonine phosphorylation of GSK-3 is high in motile compared to immotile sperm in bulls (Vijayaraghavan et al., *Biol. Reprod.*, 62, 1647 (2000)). This effect was also demonstrated with human sperm (Luconi et al., *Human Reprod.*, 16, 1931 (2001)).

Considering the lack of currently available treatment options for the majority of the conditions associated with GSK-3 protein kinase, there is still a great need for new therapeutic agents that inhibit this protein target.

SUMMARY OF THE INVENTION

It has now been found that compounds of this invention, and pharmaceutically acceptable compositions thereof, are effective as inhibitors of GSK protein kinase. These compounds have the general formula I:

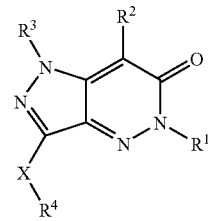

or a pharmaceutically acceptable salt or mixtures thereof, wherein $R^1$, $R^2$, $R^3$, $R^4$ and X, are as defined below.

The compounds of this invention are capable of inhibiting GSK-3 activity. According to the invention, these compounds are also utilized in compositions and methods for inhibiting GSK-3 activity and methods for treating or lessening the severity of diseases or conditions associated with GSK-3 in patients.

The diseases or conditions amenable to the methods of this invention include, for example, neurological and neurodegenerative disorders, diabetes, psychiatric disorders, multiple sclerosis (MS), myocardial infarction, reperfusion/ischemia, baldness, and stroke.

DETAILED DESCRIPTION OF THE INVENTION

I. General Description of Compounds of the Invention

The present invention relates to a compound of formula I:

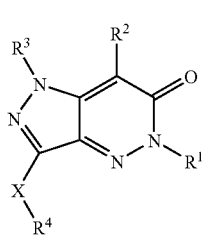

or a pharmaceutically acceptable salt or mixtures thereof,
wherein $R^1$ is selected from -$(L)_m R$, -$(L)_m Ar^1$, or -$(L)_m Cy^1$; L is an optionally substituted $C_{1-6}$ alkylidene chain wherein up to two non-adjacent methylene units of L are optionally replaced by O, NR, NRCO, NRCS, NRCONR, NRCSNR, NRCO$_2$, CO, CO$_2$, CONR, CSNR, OC(O)NR, SO$_2$, SO$_2$NR, NRSO$_2$, NRSO$_2$NR, C(O)C(O), or C(O)CH$_2$C(O); m is 0 or 1; $Ar^1$ is an optionally substituted aryl group selected from a 3-8 membered monocyclic or an 8-10 membered bicyclic ring having 0-5 heteroatoms independently selected from nitrogen, oxygen, or sulfur; and $Cy^1$ is an optionally substituted group selected from a 3-7-membered saturated or partially unsaturated monocyclic ring having 0-3 heteroatoms independently selected from nitrogen, oxygen, or sulfur, or an 8- 10-membered saturated or partially unsaturated bicyclic ring system having 0-5 heteroatoms independently selected from nitrogen, oxygen, or sulfur, wherein $Ar^1$ and $Cy^1$ are each independently optionally substituted with up to five substituents selected from Z-R$^Y$; wherein Z is a bond or is a $C_1$-$C_6$ alkylidene chain wherein up to two non-adjacent methylene units of Z are optionally replaced by CO, $CO_2$, COCO, CONR, CSNR, OCONR, NRNR, NRNRCO, NRCO, NRCS, NRCO$_2$, NRCONR, NRCSNR, SO, SO$_2$, NRSO$_2$, SO$_2$NR, NRSO$_2$NR, O, S, or NR; and each occurrence of R$^Y$ is independently selected from R', halogen, NO$_2$, CN, OR', SR', N(R')$_2$, NR'C(O)R', NR'C(S)R', NR'C(O)N(R')$_2$, NR'C(S)N(R')$_2$, NR∝CO$_2$R', C(O)R', CO$_2$R', OC(O)R', C(O)N(R')$_2$, C(S)N(R')$_2$, OC(O)N(R')$_2$, SOR', SO$_2$R', SO$_2$N(R')$_2$, NR'SO$_2$R', NR'SO$_2$N(R')$_2$, C(O)C(O)R', or C(O)CH$_2$C(O)R';

R$^2$ is selected from halogen, NO$_2$, CN, —SR, —N(R)$_2$, -(T)$_n$R, or -(T)$_n$Ar$^2$ wherein T is an optionally substituted $C_{1-4}$ alkylidene chain wherein up to two non-adjacent methylene units of T are optionally replaced by O, NR, NRCO, NRCS, NRCONR, NRCSNR, NRCO$_2$, CO, CO$_2$, CONR, CSNR, OC(O)NR, SO$_2$, SO$_2$NR, NRSO$_2$, NRSO$_2$NR, C(O)C(O), or C(O)CH$_2$C(O); n is 0 or 1; Ar$^2$ is an optionally substituted aryl group selected from a 5-6 membered monocyclic or an 8-10 membered bicyclic ring having 0-5 heteroatoms independently selected from nitrogen, oxygen, or sulfur wherein Ar$^2$ is independently optionally substituted with up to five substituents selected from Q-R$^X$; wherein Q is a bond or is a $C_1$-$C_6$ alkylidene chain wherein up to two non-adjacent methylene units of Q are optionally replaced by CO, CO$_2$, COCO, CONR, CSNR, OCONR, NRNR, NRNRCO, NRCO, NRCS, NRCO$_2$, NRCONR, NRCSNR, SO, SO$_2$, NRSO$_2$, SO$_2$NR, NRSO$_2$NR, O, S, or NR; and each occurrence of R$^X$ is independently selected from R', halogen, NO$_2$, CN, OR', SR', N(R')$_2$, NR'C(O)R', NR'C(S)R', NR'C(O)N(R')$_2$, NR'C(S)N(R')$_2$, NR'CO$_2$R', C(O)R', CO$_2$R', OC(O)R', C(O)N(R')$_2$, C(S)N(R')$_2$, OC(O)N(R')$_2$, SOR', S$_2$R', SO$_2$N(R')$_2$, NR'SO$_2$R', NR'SO$_2$N(R')$_2$, C(O)C(O)R', or C(O)CH$_2$C(O)R';

R$^3$ is hydrogen or an optionally substituted $C_{1-4}$ aliphatic group;

X is selected from a valence bond, O, S, or NR;

R$^4$ is selected from —R, —(U)$_j$Ar$^3$, or —(U)$_j$Cy$^3$; U is an optionally substituted $C_{1-6}$ alkylidene chain wherein up to two non-adjacent methylene units of U are optionally replaced by O, NR, NRCO, NRCS, NRCONR, NRCSNR, NRCO$_2$, CO, CO$_2$, CONR, CSNR, OC(O)NR, SO$_2$, SO$_2$NR, NRSO$_2$, NRSO$_2$NR, C(O)C(O), or C(O)CH$_2$C(O); j is 0 or 1; Ar$^3$ is an optionally substituted aryl group selected from a 3-8 membered monocyclic or an 8-10 membered bicyclic ring having 0-5 heteroatoms independently selected from nitrogen, oxygen, or sulfur; and Cy$^3$ is an optionally substituted group selected from a 3-7-membered saturated or partially unsaturated monocyclic ring having 0-3 heteroatoms independently selected from nitrogen, oxygen, or sulfur, or an 8-10-membered saturated or partially unsaturated bicyclic ring system having 0-5 heteroatoms independently selected from nitrogen, oxygen, or sulfur, wherein Ar$^3$ and Cy$^3$ are each independently optionally substituted with up to five substituents selected from Y—R$^Z$; wherein Y is a bond or is a $C_1$-$C_6$ alkylidene chain wherein up to two non-adjacent methylene units of Y are optionally replaced by CO, CO$_2$, COCO, CONR, CSNR, OCONR, NRNR, NRNRCO, NRCO, NRCS, NRCO$_2$, NRCONR, NRCSNR, SO, SO$_2$, NRSO$_2$, SO$_2$NR, NRSO$_2$NR, O, S, or NR; and each occurrence of R$^Z$ is independently selected from R', halogen, NO$_2$, CN, OR', SR', N(R')$_2$, NR'C(O)R', NR'C(S)R', NR'C(O)N(R')$_2$, NR'C(S)N(R')$_2$, NR'CO$_2$R', C(O)R', CO$_2$R', OC(O)R', C(O)N(R')$_2$, C(S)N(R')$_2$, OC(O)N(R')$_2$, SOR', SO$_2$R', SO$_2$N(R')$_2$, NR'SO$_2$R', NR'SO$_2$N(R')$_2$, C(O)C(O)R', or C(O)CH$_2$C(O)R'; or wherein R$^4$ and R, taken together with the nitrogen form an optionally substituted 5-8 membered heterocyclyl or heteroaryl ring having 1-3 heteroatoms independently selected from nitrogen, oxygen, or sulfur;

each occurrence of R is independently selected from hydrogen or an optionally substituted $C_{1-6}$ aliphatic group, or two R on the same nitrogen are taken together with the nitrogen to form a 5-8 membered heterocyclyl or heteroaryl ring having 1-3 heteroatoms independently selected from nitrogen, oxygen, or sulfur; and each occurrence of R' is independently selected from hydrogen or an optionally substituted group selected from $C_{1-6}$ aliphatic, $C_{6-10}$ aryl, a heteroaryl ring having 5-10 ring atoms, or a heterocyclyl ring having 3-10 ring atoms, or wherein two R on the same nitrogen are taken together with the nitrogen to form a 5-8 membered heterocyclyl or heteroaryl ring having 1-3 heteroatoms independently selected from nitrogen, oxygen, or sulfur.

In certain embodiments, for compounds of formula I one or more, or all of the following conditions apply:
a) when X is NR; R, R$^3$, and R$^4$ are each hydrogen; R$^2$ is -(T)$_n$R wherein n is zero and R is hydrogen; and R$^1$ is -(L)$_m$Ar$^1$ wherein m is 0; then Ar$^1$ is not:
   i) 4-Cl or 4-OMe phenyl; or
   ii) 3-CF$_3$ phenyl;
b) when X is NR; R and R$^3$ are each hydrogen; R$^2$ is -(T)$_n$R wherein n is 0 and R is hydrogen; R$^4$ is 2-phenyl-4-quinazolinyl; and R$^1$ is -(L)$_m$Ar$^1$ wherein m is 0; then Ar$^1$ is not:
   i) phenyl, 3-OMe phenyl, 4-OMe phenyl, 2,4-diCl phenyl, 4-Cl phenyl, 3-CF$_3$ phenyl, or 4-OPh phenyl;
c) when X is NR; R and R$^3$ are each hydrogen; R$^2$ is -(T)$_n$R wherein n is 0 and R is hydrogen; R$^4$ is 2-(2-trifluoromethyl-phenyl)-4-quinazolinyl; and R$^1$ is -(L)$_m$Ar$^1$ wherein m is 0; then Ar$^1$ is not phenyl.
d) when X is a valence bond; R$^4$ is hydrogen; R$^3$ is CH$_3$; R$^2$ is either chloro or hydrogen; and R$^1$ is -(L)$_m$Ar$^1$ wherein m is 0, then Ar$^1$ is not 3-trifluoromethyl phenyl or 2-fluoro-5-trifluoromethyl phenyl.
e) when X is a valence bond; R$^4$ is methyl; R$^3$ is hydrogen; and R$^2$ is cyano, then R$^1$ is not phenyl.
f) when X is a valence bond; R$^4$ is methyl; R$^2$ is -(T)$_n$R wherein n is 0 and R is hydrogen; R$^3$ is hydrogen; and R$^1$ is -(L)$_m$Ar$^1$ wherein m is 0; then Ar$^1$ is not 4-tolyl.
g) when X is a valence bond; R$^4$ is methyl; R$^3$ is hydrogen; and R$^1$ is -(L)$_m$Ar$^1$ wherein m is 0; and Ar$^1$ is substituted phenyl; then R$^2$ is not 4-nitrophenoxy.
h) when X is a valence bond; R$^3$ is hydrogen; R$^2$ is -(T)$_n$R wherein n is 0 and R is hydrogen; R$^1$ is -(L)$_m$Ar$^1$ wherein m is 0; and Ar$^1$ is 2-pyridyl or 4-Cl phenyl; then R$^4$ is not phenyl with an amide in the para position.

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The terms "alkyl", "alkenyl" and "alkynyl" used alone or as part of a larger moiety shall include both straight and branched chains containing one to four carbon atoms and at least two carbon atoms and one double bond in the case of alkenyl and at least two carbon atoms and one triple bond, in the case of alkynyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halogen; —R°; —OR°; —SR°; 1,2-methylenedioxy; 1,2-ethylenedioxy; phenyl (Ph) optionally substituted with R°; —O(Ph) optionally substituted with R°; —(CH$_2$)$_{1-2}$(Ph), optionally substituted with R°; —CH═CH(Ph), optionally substituted with R°; —NO$_2$; —CN; —N(R°)$_2$; —NR°C(O)R°; —NR°C(S) R°; —NR°C(O)N(R°)$_2$; —NR°C(S)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —C(O)R°; —C(S)R°; —C(O)N(R°)$_2$; —C(S)N (R°)$_2$; —OC(O)N(R°)$_2$; —OC(O)R°; —C(O)N(OR°)R°; —C(NOR°)R°; —S(O)$_2$R°; —S(O)$_3$R°; —SO$_2$N(R°)$_2$; —S(O)R°; —NR°SO$_2$N(R°)$_2$; —NR°SO$_2$R°; —N(OR°)R°; —C(═NH)—N(R°)$_2$; or —(CH$_2$)$_{0-2}$NHC(O)R° wherein each independent occurrence of R° is selected from hydrogen, optionally substituted C$_{1-6}$ aliphatic, an unsubstituted 5-6 membered heteroaryl or heterocyclic ring, phenyl, —O(Ph), or —CH$_2$(Ph), or, notwithstanding the definition above, two independent occurrences of R°, on the same substituent or different substituents, taken together with the atom(s) to which each R° group is bound, form a 5-8-membered heterocyclyl, aryl, or heteroaryl ring or a 3-8-membered cycloalkyl ring having 0-3 heteroatoms independently selected from nitrogen, oxygen, or sulfur. Optional substituents on the aliphatic group of R° are selected from NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or haloC$_{1-4}$aliphatic, wherein each of the foregoing C$_{1-4}$aliphatic groups of R° is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O) R*, =NNHCO$_2$(alkyl), =NNHSO$_2$(alkyl), or =NR*, where each R* is independently selected from hydrogen or an optionally substituted C$_{1-6}$ aliphatic. Optional substituents on the aliphatic group of R* are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$aliphatic groups of R* is unsubstituted.

Optional substituents on the nitrogen of a non-aromatic heterocyclic ring are selected from —R$^+$, —N(R$^+$)$_2$, —C(O) R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N (R$^-$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$ (Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with the atom(s) to which each R$^+$ group is bound, form a 5-8-membered heterocyclyl, aryl, or heteroaryl ring or a 3-8-membered cycloalkyl ring having 0-3 heteroatoms independently selected from nitrogen, oxygen, or sulfur. Optional substituents on the aliphatic group or the phenyl ring of R$^+$ are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$aliphatic groups of R$^+$ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of R° (or R$^+$, or any other variable similarly defined herein), are taken together together with the atom(s) to which each variable is bound to form a 5-8-membered heterocyclyl, aryl, or heteroaryl ring or a 3-8-membered cycloalkyl ring having 0-3 heteroatoms independently selected from nitrogen, oxygen, or sulfur. Exemplary rings that are formed when two independent occurrences of R° (or R$^+$, or any other variable similarly defined herein) are taken together with the atom(s) to which each variable is bound include, but are not limited to the following: a) two independent occurrences of R° (or R$^+$, or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R$^+$, or any other variable similarly defined herein) that are bound to different atoms and are taken together with both of those atoms to form a ring, for example where a phenyl group is substituted with two occurrences of OR°

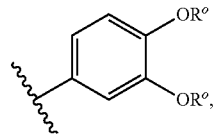

these two occurrences of R° are taken together with the oxygen atoms to which they are bound to form a fused 6-membered oxygen containing ring:

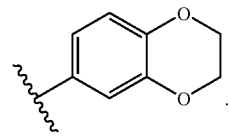 [SMILES: *c1ccc2c(c1)OCCO2 ; "."]

It will be appreciated that a variety of other rings can be formed when two independent occurrences of R° (or R$^+$, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention.

II. Embodiments

As described generally above, in certain embodiments, R$^1$ is -(L)$_m$Ar$^1$, -(L)$_m$R, or -(L)$_m$Cy$^1$. In another embodiment, R$^1$ is -(L)$_m$Ar$^1$ and compounds have the general formula IA:

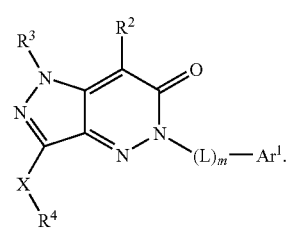

IA

In another embodiment, where R$^1$ is -(L)$_m$Ar$^1$, Ar$^1$ is selected from one of the following groups:

1-1 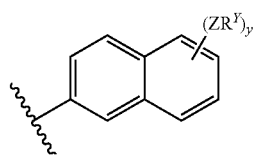
1-2 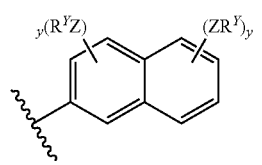
1-3 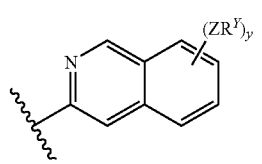
1-4 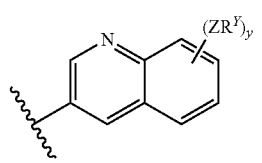
1-5 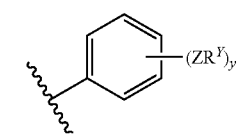
1-6 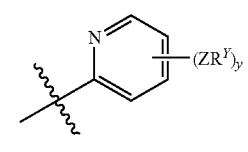
1-7 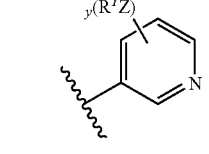
1-8 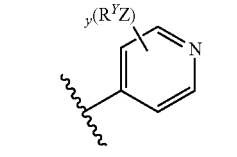
1-9 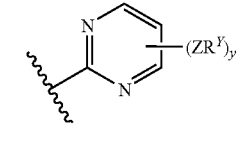
1-10 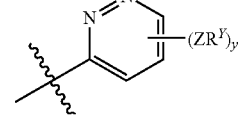
1-11 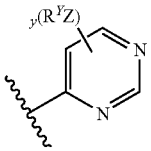
1-12 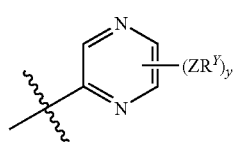
1-13 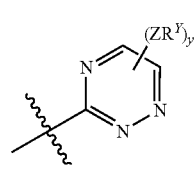
1-14 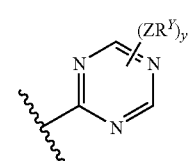
1-15 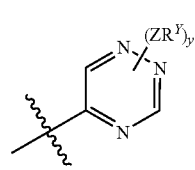
1-16 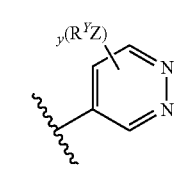
1-17 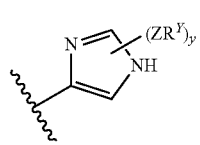
1-18 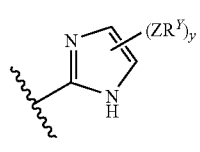
1-19 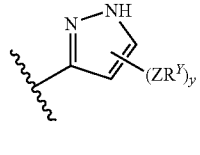
1-20 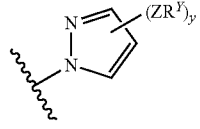

1-21 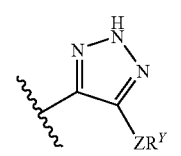
1-22 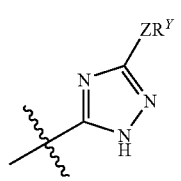
1-23 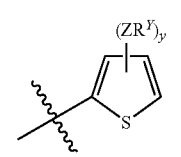
1-24 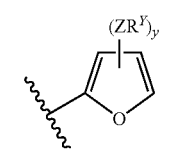
1-25 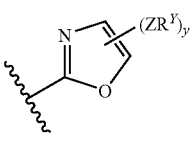
1-26 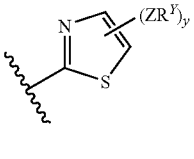
1-27 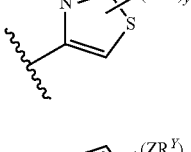
1-28 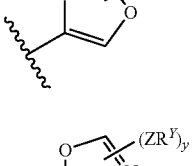
1-29 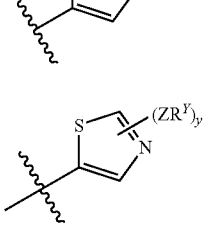
1-30 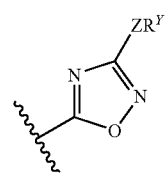
1-31 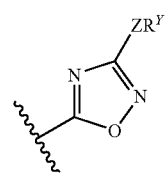
1-32 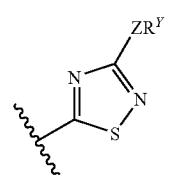
1-33 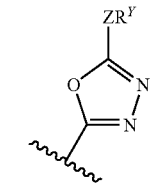
1-34 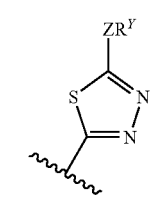
1-35 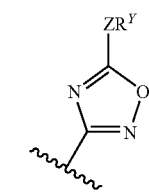
1-36 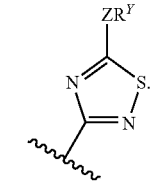
In another embodiment, $Ar^1$ is selected from one of the following groups:
1-5 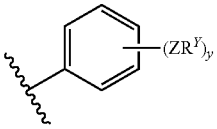
1-6 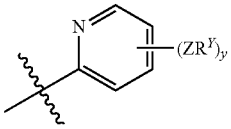

1-7
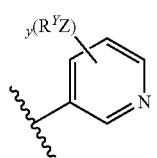
1-8
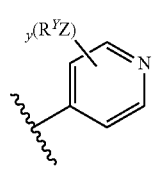
1-9
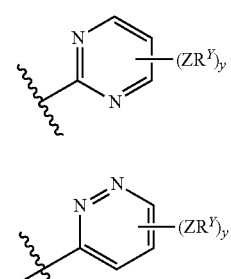
1-10
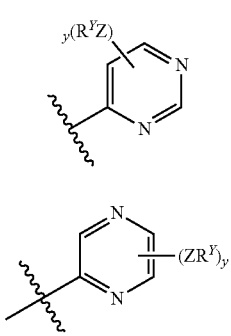
1-11
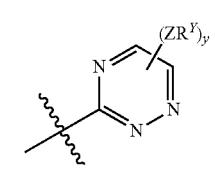
1-12
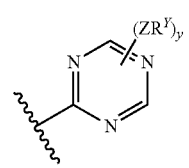
1-13
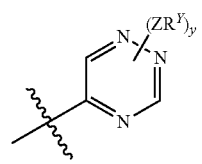
1-14
1-15
1-16
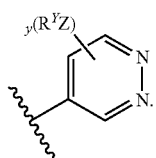
In another embodiment, $Ar^1$ is selected from one of the following groups:
1-5
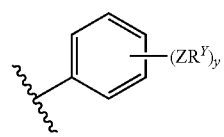
1-6
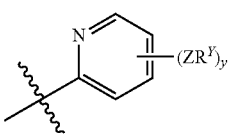
1-7
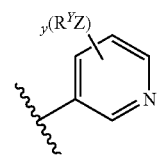
1-8
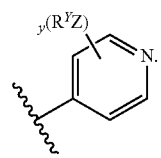
In certain other embodiments, $R^1$ is $-(L)_m-Cy^1$ and compounds have the general formula IA-2:
IA-2
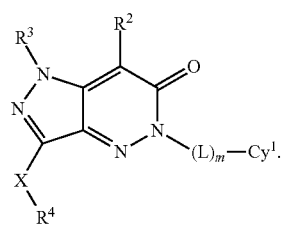
In another embodiment $Cy^1$ is selected one of the following groups:
2-1
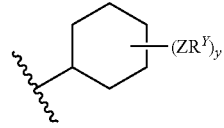

-continued

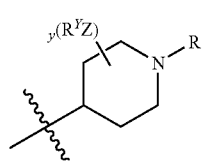
2-2

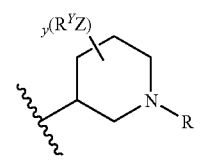
2-3

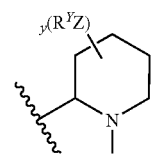
2-4

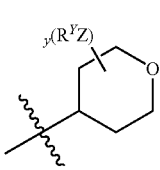
2-5

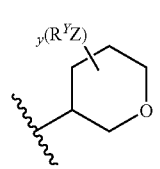
2-6

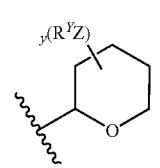
2-7

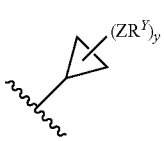
2-8

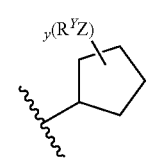
2-9

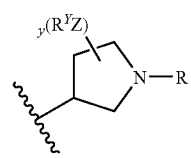
2-10

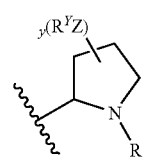
2-11

-continued

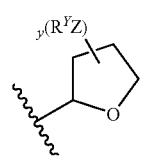
2-12

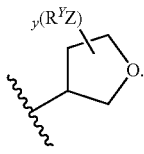
2-13

In another embodiment, $R^1$ is $-(L)_m-Ar^1$, m is 1 and compounds have the formula IA-3:

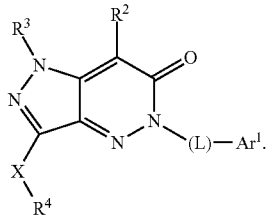
IA-2

In another embodiment $Ar^1$ is phenyl substituted with 0-3 occurrences of $ZR^Y$ and compounds have the general formula IA-1-5:

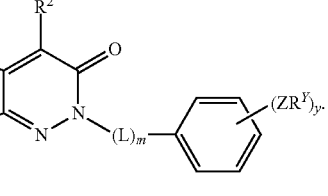
IA-1-5

For each of the subsets described above, L is an optionally substituted $C_{1-6}$ straight or branched alkylidene chain wherein up to 2 non-adjacent methylene units of L are optionally replaced by O, NR, NRCO, NRCS, NRCONR, NRCSNR, NRCO$_2$, CO, CO$_2$, CONR, CSNR, OC(O)NR, SO$_2$, SO$_2$NR, NRSO$_2$, NRSO$_2$NR, C(O)C(O), or C(O)CH$_2$C(O) and m is 1.

In other embodiments, L is an optionally substituted $C_{1-6}$ straight or branched alkylidene chain wherein one methylene unit of L is optionally replaced by CO, CO$_2$, CONR, CSNR, SO$_2$NR, and m is 1.

In yet other embodiments, compounds of formula I and subsets thereof include those compounds wherein $R^1$ is $-(L)_m$ R, L is an optionally substituted $C_{1-6}$ straight or branched alkylidene chain wherein one methylene unit of L is optionally replaced by O, NR, NRCO, NRCS, NRCONR, NRCSNR, NRCO$_2$, CO, CO$_2$, CONR, CSNR, OC(O)NR, SO$_2$, SO$_2$NR, NRSO$_2$, NRSO$_2$NR, C(O)C(O), or C(O)CH$_2$C(O), R is an optionally substituted $C_{1-6}$ aliphatic group, and m is 1.

As described generally above, in certain embodiments, $R^2$ is selected from halogen, NO$_2$, CN, —SR, —N(R)$_2$, or $-(T)_n$ R, wherein R is selected from hydrogen or an optionally substituted $C_{1-6}$ aliphatic group, or two R on the same nitrogen are taken together with the nitrogen to form a 5-8 membered heterocyclyl or heteroaryl ring having 1-3 heteroatoms independently selected from nitrogen, oxygen, or sulfur.

In another embodiment, $R^2$ is selected from —$N(R)_2$, or -$(T)_nR$, wherein n is 0, and R is selected from hydrogen or an optionally substituted $C_{1-6}$ aliphatic group.

In another embodiment, $R^2$ is -$(T)_nR$, wherein n is 0, and R is selected from hydrogen, $CH_3$, or $CF_3$.

In yet another embodiment, $R^2$ is -$(T)_nR$, wherein n is 0, R is hydrogen, and compounds have the formula IB:

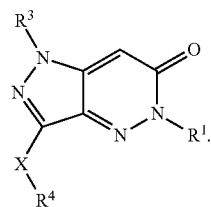

IB

As described generally above, in certain embodiments, $R^3$ is hydrogen, methyl, ethyl, propyl, or isopropyl.

In certain other embodiments, $R^3$ is hydrogen or methyl.

In another embodiment, $R^3$ is hydrogen and compounds have the formula IC:

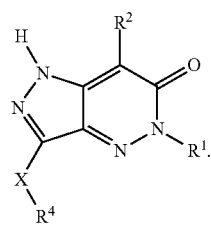

IC

As described generally above, in certain embodiments, X is selected from a valence bond or NR. In certain other embodiments, X is NR and R is hydrogen.

In another embodiment, X is NR, R is hydrogen, and compounds have the formula ID:

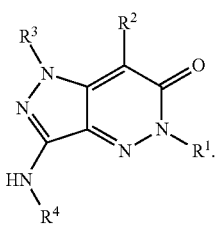

ID

In certain other embodiments, X is $OR^4$ and compounds have the formula IE:

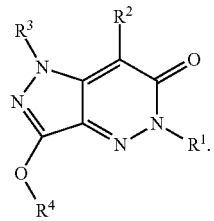

IE

In yet other embodiments, X is $SR^4$ and compounds have the formula IF:

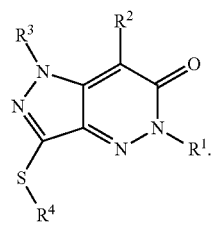

IF

As described generally above, in certain other embodiments, $R^4$ is —$(U)_jAr^3$, —$(U)_jR$, or —$(U)_jCy^3$.

In yet other embodiments, $R^4$ is —$(U)_jAr^3$ and compounds have the general formula IG:

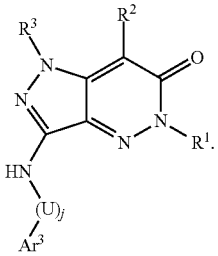

IG

In another embodiment, $R^4$ is —$(U)_jAr^3$, and $Ar^3$ is selected from one of the following groups:

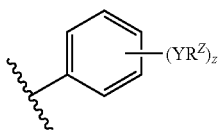

1-5-a

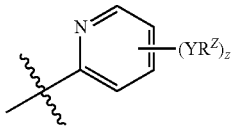

1-6-a

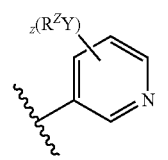 1-7-a
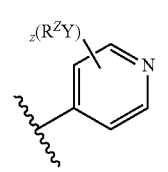 1-8-a
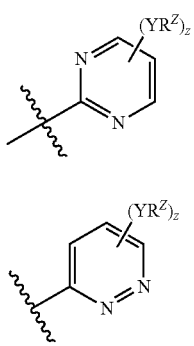 1-9-a
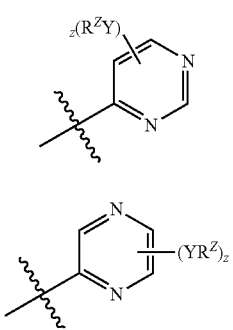 1-10-a
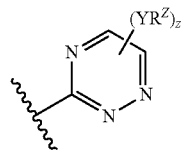 1-11-a
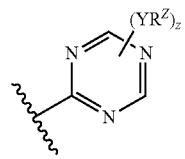 1-12-a
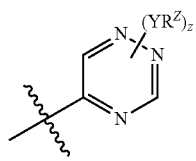 1-13-a
1-14-a
1-15-a
1-16-a
1-37
1-38
In other embodiments, Ar³ is selected from one of the following groups:
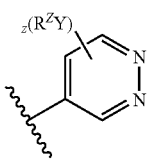 1-5-a
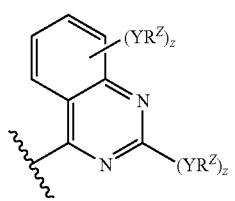 1-6-a
1-7-a
1-8-a
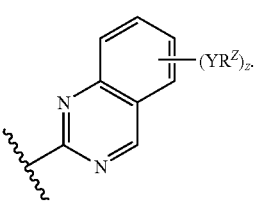 1-9-a -continued
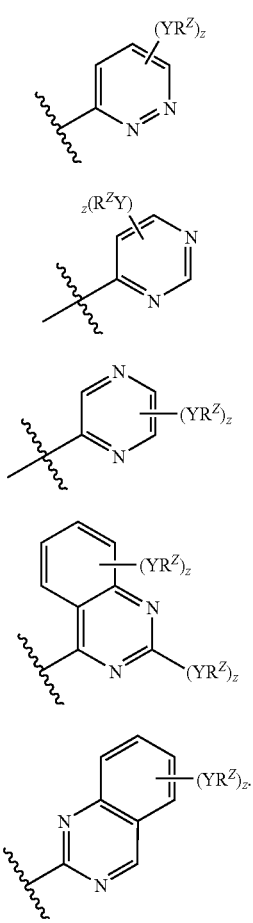
1-10-a
1-11-a
1-12-a
1-37
1-38
In other embodiments, Ar³ is selected from one of the following groups:
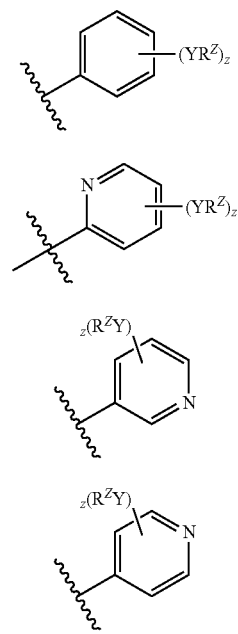
1-5-a
1-6-a
1-7-a
1-8-a
-continued
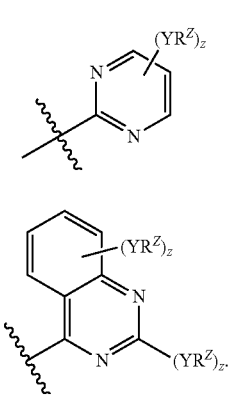
1-9-a
1-37
In another embodiment, $R^4$ is $-(U)_jAr^3$, and $Ar^3$ is selected from one of the following groups:
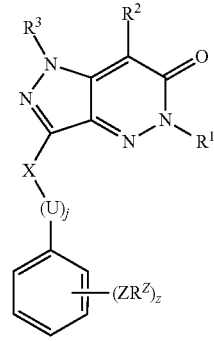
IH
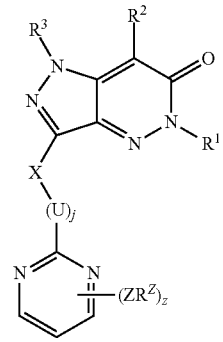
IJ
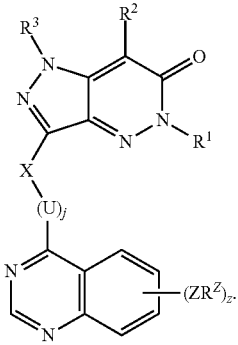
IK In certain other embodiments, R⁴ is —(U)ⱼCy³ and compounds have the general formula IG-1:
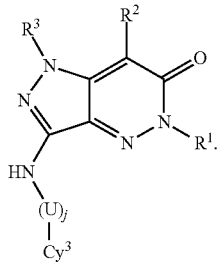
IG-1
In other embodiments, Cy³ is selected from one of the following groups:
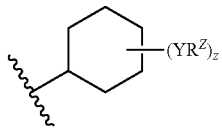
2-1
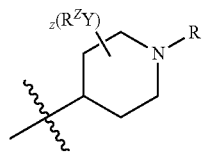
2-2
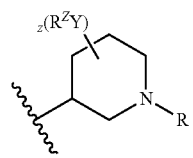
2-3
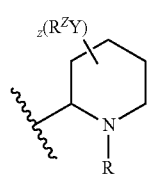
2-4
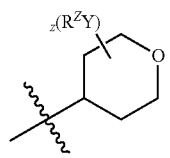
2-5
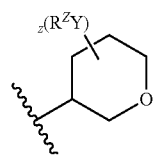
2-6
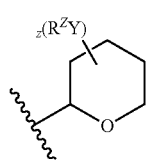
2-7
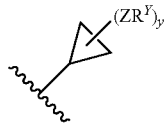
2-8
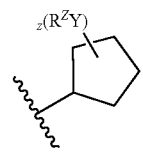
2-9
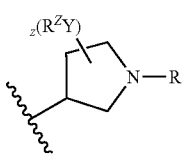
2-10
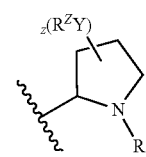
2-11
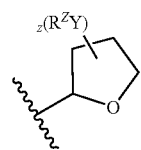
2-12
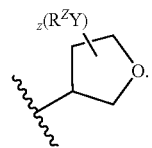
2-13
In certain other embodiments, X is NR wherein R is hydrogen, R⁴ is hydrogen, and compounds have the formula IL:
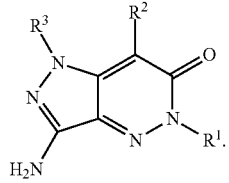
IL
In yet other embodiments, X is a valence bond and compounds have the formula IM:
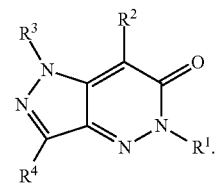
IM In still other embodiments, $R^4$ is R and R is an optionally substituted $C_{1-6}$ aliphatic group.

As described generally above, in certain embodiments of compounds of formula I, y is 0-5, and $Ar^1$ and $Cy^1$ are independently substituted with 0-5 occurrences of $ZR^Y$. Additionally, $Ar^3$ and $Cy^3$ are independently substituted with 0-5 occurrences of $YR^Z$. In certain other embodiments for compounds of formula I and subsets thereof, each occurrence of $ZR^Y$ and $YR^Z$ is independently halogen, $NO_2$, CN, or an optionally substituted group selected from $C_{1-4}$ aliphatic, aryl, aralkyl, —N(R')$_2$, —CH$_2$N(R')$_2$, —OR', —CH$_2$OR', —SR', —CH$_2$SR', —COOR', or —S(O)$_2$N(R')$_2$. In yet other embodiments, each occurrence of $ZR^Y$ and $YR^Z$ is independently Cl, $CF_3$, $NO_2$, —S(O)$_2$N(R')$_2$ or an optionally substituted group selected from $C_{1-4}$ alkoxy, phenyl, phenyloxy, benzyl, or benzyloxy.

In another embodiment of compounds of formula I, y is 0, and $Ar^1$ is unsubstituted.

In other embodiments, $R^1$ is -(L)$_m$Ar$^1$, m is 0 or 1, $Ar^1$ is phenyl optionally substituted with 0-5 occurrences of $ZR^Y$, and compounds have the formula IIA or IIA-1:

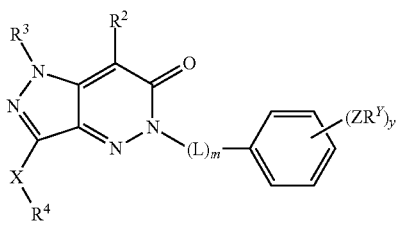

IIA

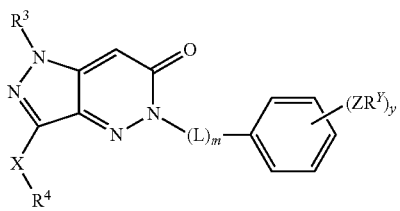

IIA-1

In certain other embodiments, $R^2$ is -(T)$_n$R, wherein n is 0 and R is hydrogen, $R^1$ is -(L)$_m$Ar$^1$, wherein m is 0 or 1, $Ar^1$ is phenyl optionally substituted with 0-5 occurrences of $ZR^Y$, and compounds have the formula IIB or IIB-1:

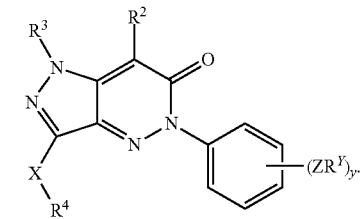

IIB

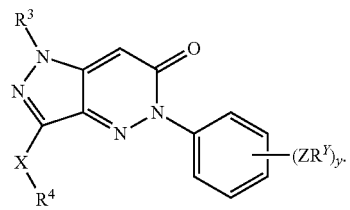

IIB-1

In other embodiments, $R^2$ is -(T)$_n$R, wherein n is 0 and R is hydrogen, $R^3$ is hydrogen, $R^1$ is -(L)$_m$Ar$^1$ wherein m is 0 or 1, $Ar^1$ is phenyl optionally substituted with 0-5 occurrences of $ZR^Y$, and compounds have the formula IIC or IIC-1:

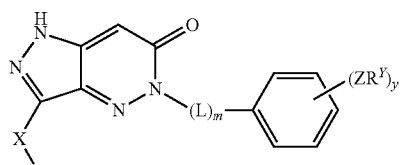

IIC

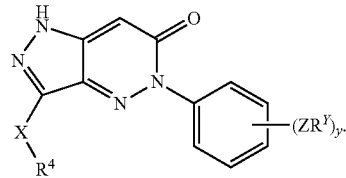

IIC-1

In yet other embodiments, $R^3$ is hydrogen, $R^2$ is -(T)$_n$R, wherein n is 0 and R is hydrogen, X is NR, $R^1$ is -(L)$_m$Ar$^1$ wherein m is 0 or 1, $Ar^1$ is phenyl optionally substituted with 0-5 occurrences of $ZR^Y$, and compounds have the formula IID or IID-1:

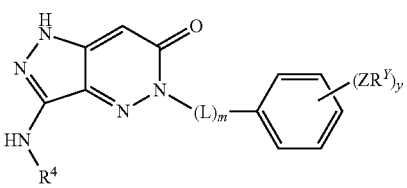

IID

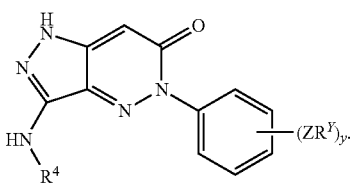

IID-1

In still other embodiments, $R^3$ is hydrogen, $R^2$ is -(T)$_n$R, wherein n is 0 and R is hydrogen, $R^1$ is -(L)$_m$Ar$^1$ wherein m is 0 or 1, $Ar^1$ is phenyl optionally substituted with 0-5 occurrences of $ZR^Y$, and compounds have the formula IIE, IIE-1, IIF, IIF-1, IIG, or IIG-1:

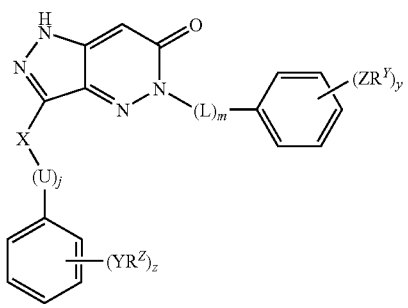
IIE
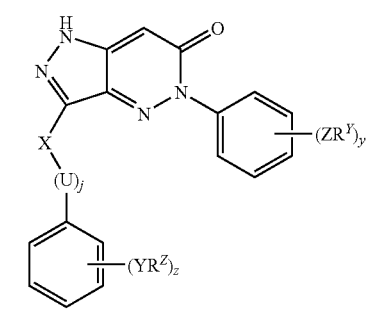
IIE-1
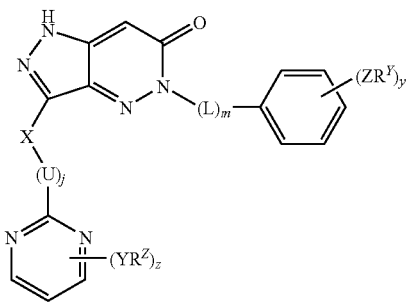
IIF
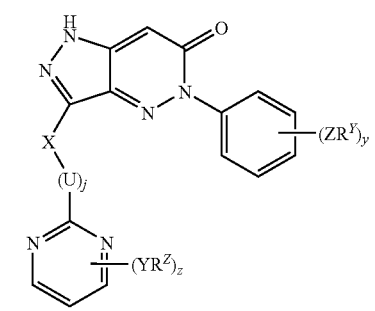
IIF-1
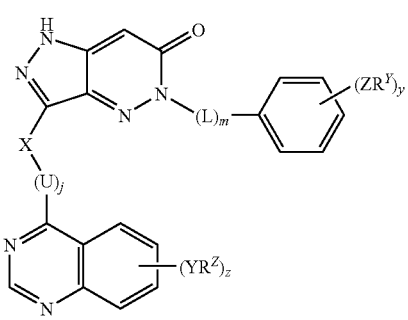
IIG
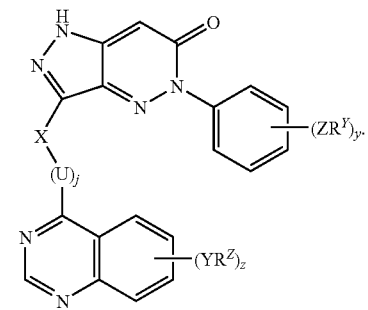
IIG-1
In certain other embodiments, $R^3$ is hydrogen, $R^2$ is -(T)$_n$R, wherein n is 0 and R is hydrogen, X is NH, $R^1$ is -(L)$_m$Ar$^1$ wherein m is 0 or 1, Ar$^1$ is phenyl optionally substituted with 0-5 occurrences of ZR$^Y$, and compounds have the formula IIIE, IIIE-1, IIIF, IIIF-1, IIIG, or IIIG-1:
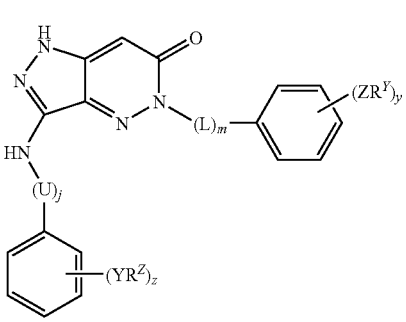
IIIE
IIIE-1
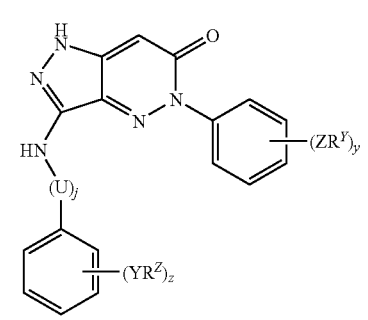
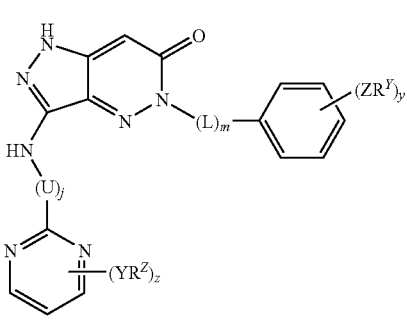
IIIF -continued

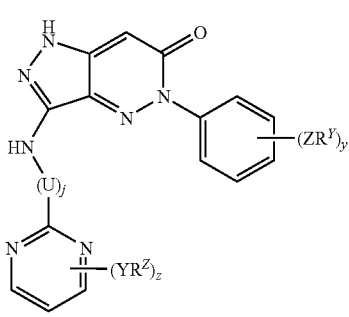

IIIF-1

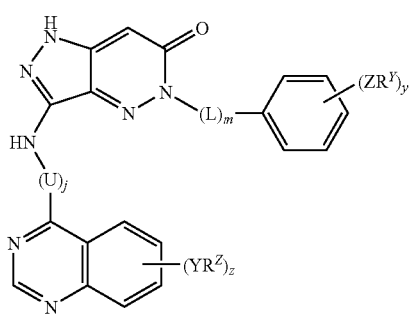

IIIG

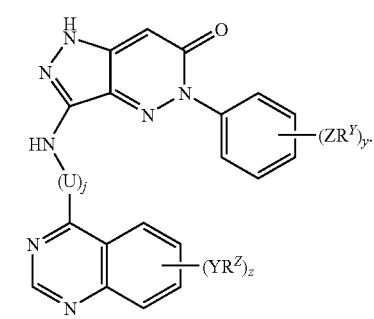

IIIG-1

In still other embodiments, R³ and R⁴ are hydrogen, R² is -(T)$_n$R, wherein n is 0 and R is hydrogen, X is NR, Ar¹ is optionally substituted phenyl, R¹ is -(L)$_m$Ar¹, and compounds have the formula IIH or IIH-1:

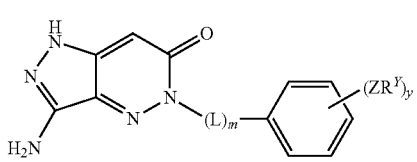

IIH

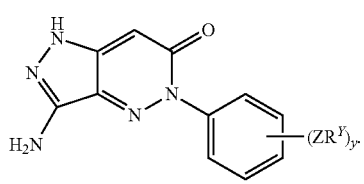

IIH-1

In other embodiments, R³ and R⁴ are hydrogen, R² is -(T)$_n$R, wherein n is 0 and R is hydrogen, X is a valence bond, Ar¹ is optionally substituted phenyl, R¹ is -(L)$_m$Ar¹, and compounds have the formula IIJ or IIJ-1:

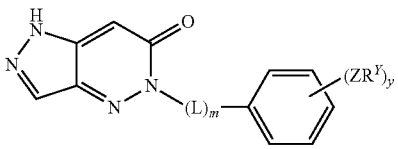

IIJ

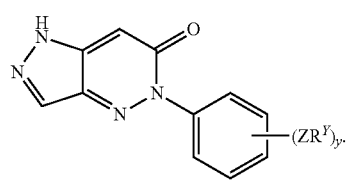

IIJ-1

In another embodiment, certain subclasses of the foregoing compounds IIA, IIA-1, IIB, IIB-1, IIC, IIC-1, IID, IID-1, IIE, IIE-1, IIF, IIF-1, IIG, IIG-1, IIH, IIH-1, IIJ, IIJ-1, IIIE, IIIE-1, IIIF, IIIF-1, IIIG, or IIIG-1 are of interest.

For example, in certain embodiments, for compounds described above, Ar¹ is phenyl optionally substituted with 0-5 occurrences of ZR$^Y$ or Ar¹ is pyridyl optionally substituted with 0-3 occurrences of ZR$^Y$. In other embodiments, m is 0 or m is 1 and L is CH₂; y is 0-3; and each occurrence of ZR$^Y$ is independently halogen, NO₂, CN, or an optionally substituted group selected from C$_{1-4}$ aliphatic, aryl, aralkyl, —N(R')₂, —CH₂N(R')₂, —OR', —CH₂OR', —SR', —CH₂SR', —COOR', or —S(O)₂N(R')₂. In other embodiments, each occurrence of ZR$^Y$ is independently Cl, CF₃, NO₂, —S(O)₂N(R')₂ or an optionally substituted group selected from C$_{1-4}$ alkoxy, phenyl, phenyloxy, benzyl, or benzyloxy.

For compounds of formula IIA, IIA-1, IIB, IIB-1, IIC, IIC-1, IID, IID-1, IIE, IIE-1, IIF, IIF-1, IIG, IIG-1, IIIE, IIIE-1, IIIF, IIIF-1, IIIG, or IIIG-1, Ar³ is pyridyl or pyrimidinyl each optionally substituted with 0-3 occurrences of YR$^Z$ or phenyl or quinazolyl each optionally substituted with 0-5 occurrences of YR$^Z$. In other embodiments, for compounds described above, j is 0 or j is 1 and U is CH₂; X is NH; m is 0 or m is 1 and L is CH₂; y is 0-5; and each occurrence of ZR$^Y$ or YR$^Z$ are each independently halogen, NO₂, CN, or an optionally substituted group selected from C$_{1-4}$ aliphatic, aryl, aralkyl, —N(R')₂, —CH₂N(R')₂, —OR', —CH₂OR', —SR', —CH₂SR', —COOR', or —S(O)₂N(R')₂.

It is understood that all combinations and subcombinations of embodiments, as described herein, are within the scope of the present invention.

Representative examples of compounds of formula I are set forth below in Table 1.

TABLE 1

Examples of Compounds of Formula I:

TABLE 1-continued

Examples of Compounds of Formula I:

TABLE 1-continued
Examples of Compounds of Formula I:
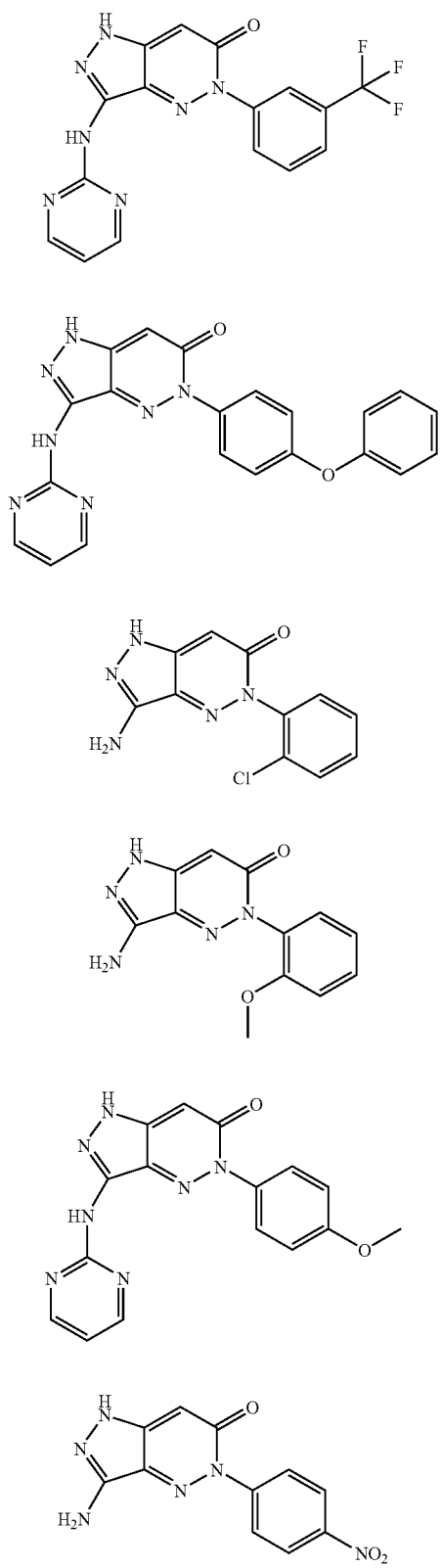
I-13
I-14
I-15
I-16
I-17
I-18
TABLE 1-continued
Examples of Compounds of Formula I:
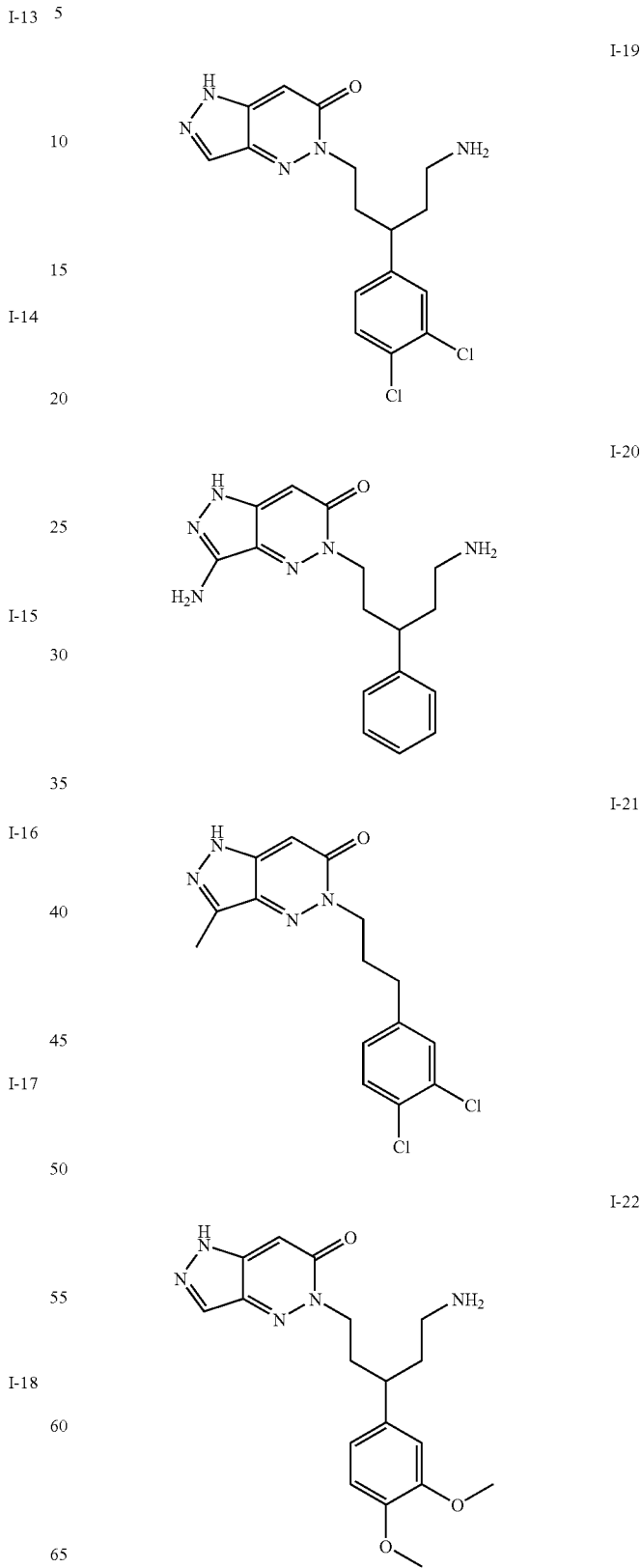
I-19
I-20
I-21
I-22

TABLE 1-continued
Examples of Compounds of Formula I:
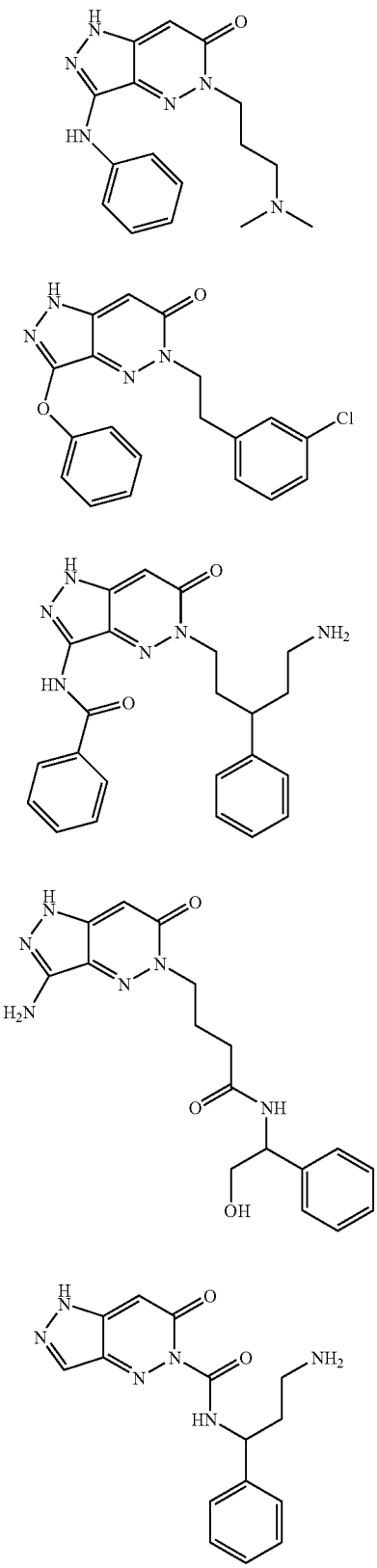
I-23
I-24
I-25
I-26
I-27
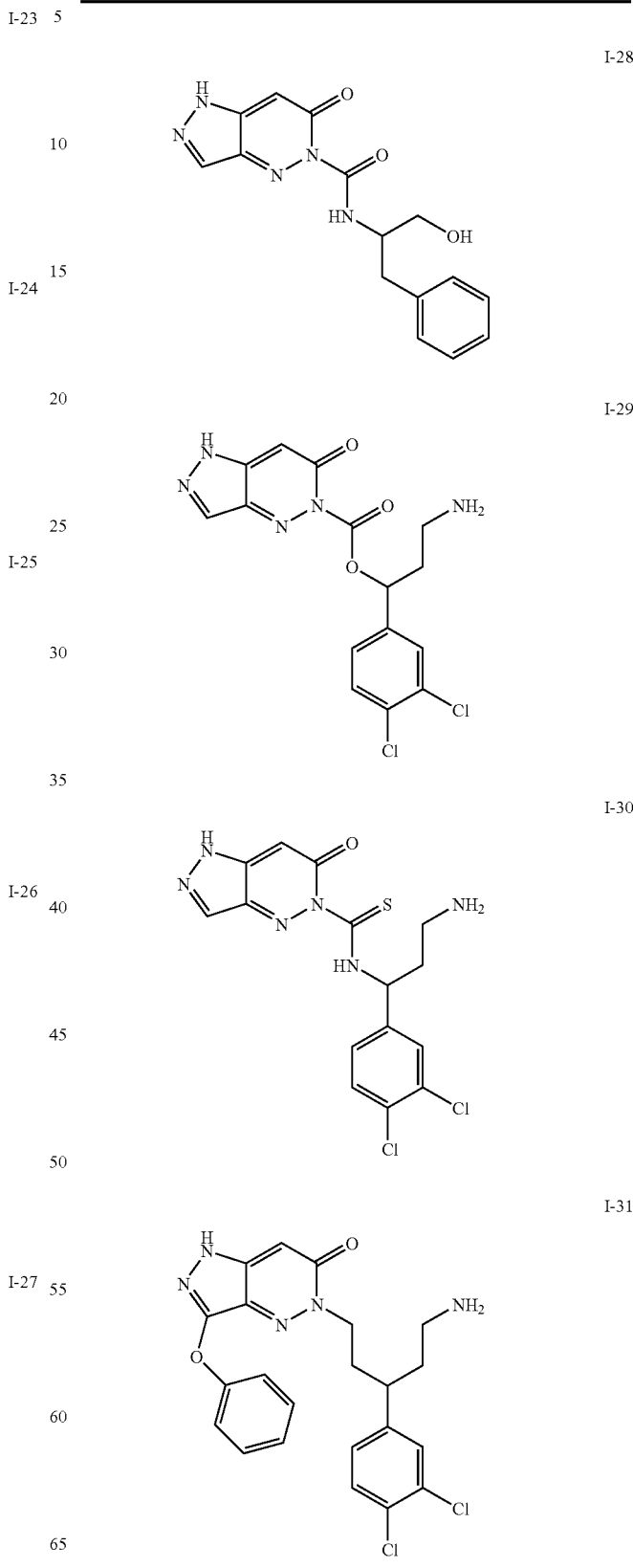
I-28
I-29
I-30
I-31

TABLE 1-continued

Examples of Compounds of Formula I:

I-32
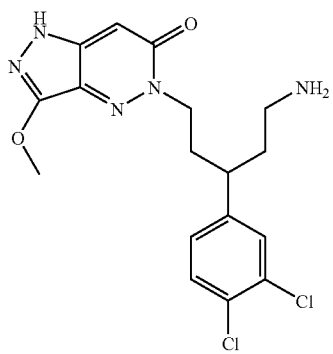

I-33
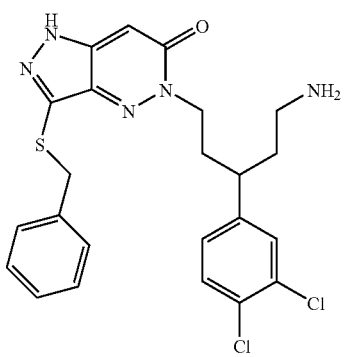

I-34
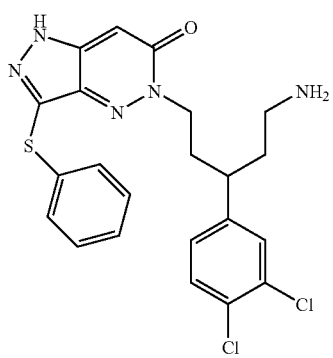

I-35
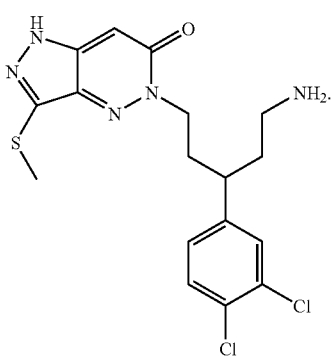

III. General Synthetic Methodology

The compounds of this invention may be prepared in general by methods known to those skilled in the art for analogous compounds. Schemes 1-7 below illustrate synthetic routes to the compounds of the present invention. Other equivalent schemes, which will be readily apparent to the ordinary skilled organic chemist, may alternatively be used to synthesize various portions of the molecule as illustrated by the general scheme below, and the preparative examples that follow.

Scheme 1:

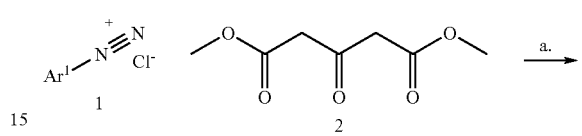

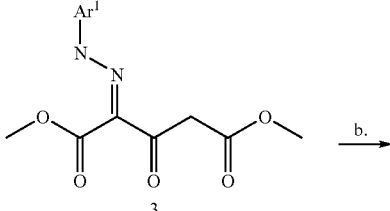

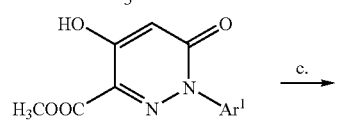

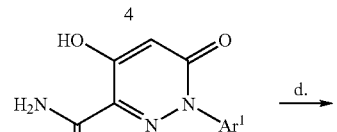

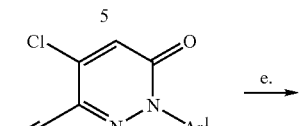

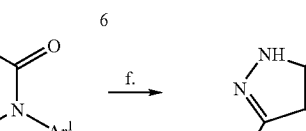

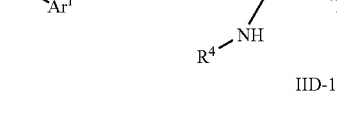

Reagents: (a) NaOAc, EtOH, $H_2O$; (b) dichlorobenzene, reflux; (c) 7N $NH_3$ in MeOH; (d) $POCl_3$, $CH_3CN$, reflux; (e) $H_2NNH_2$—$H_2O$, EtOH, 100°; (f) $Ar^3$—X or $R^4$—X, where X=halo.

Scheme 1 above shows a general method for preparing compounds of formula II-D1. For example, intermediate 5 may be prepared according to the method of Schober et al., *J. Heterocyclic Chem.*, 26, pp. 169-176 (1989) wherein aryldiazonium chloride 1 is reacted with dimethylacetonedicarboxylate 2 to provide intermediate hydrazone 3. Thermal cyclization in refluxing dichlorobenzene provides dihydopyridazine carboxylate 4. Refluxing ammonia in methanol provides amide 5 which is dehydrated and chlorinated by refluxing in excess $POCl_3$ and acetonitrile to give intermediate 6. Treatment of 6 with excess hydrazine hydrate in reluxing ethanol yields amino pyrazolo-pyridazine 7 which is alkylated with Ar³—X or R—X according to the alkylation procedure of Kawakubo et al., *Chem. Pharm. Bull.*, 35 (6), pp. 2292-2299 (1987) or Millan et al., *Aust. J. Chem.*, 53, pp. 615-618 (2000), or Kohn et al., *J. Med. Chem.*, 34, pp. 2444-2452 (1991) or the reductive amination procedure of Taylor et al., *Tetrahedron*, 48, pp. 8089-8100 (1992) to provide compounds of formula II-D1.

Scheme 2:

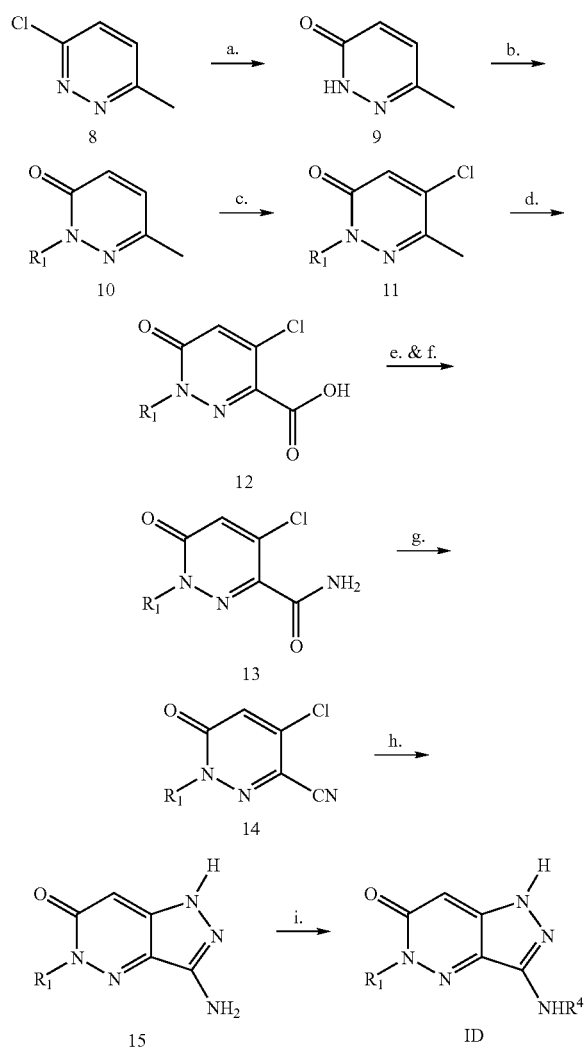

Reagents: (a) $HNO_3$; (b) $R^1(L)_mX$; (c) $Cl_2$; (d) $K_2Cr_2O_7$; (e) $(COCl)_2$; (f) $NH_3$; (g) $POCl_3$; (h) $H_2NNH_2$—$H_2O$, EtOH; (i) Ar³—X (where X=halo) or R⁴—Br.

Scheme 2 above shows a general route for the preparation of compounds of formula I wherein $R^1$ is $-(L)_mR$, X is NR, and $R^4$ is R. The preparation of intermediate acid 12 from commercially available chloropyrimidine 8 is accomplished according to the procedure of Homer et al., *J. Chem Soc.*, p. 2191 (1948). Intermediate acid 12 is converted to the amide 13 via the acid chloride and displacement with ammonia. Amino pyrazolo-pyridazine 15 is prepared as shown in Scheme 1 and finally alkylation of 15 is accomplished by those procedures described above in Scheme 1 to give compounds of formula ID.

Scheme 3:

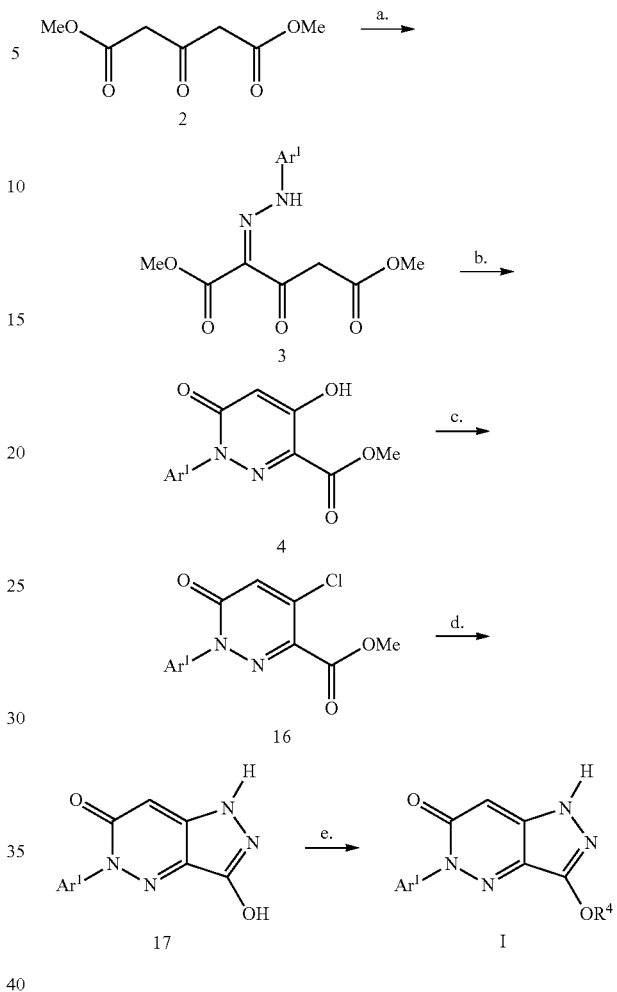

Reagents: (a) Ar¹—$N_2^+Cl^-$, NaOAc, EtOH, $H_2O$; (b) dichlorobenzene, reflux; (c) $POCl_3$, $CH_3CN$, reflux; (d) $H_2NNH_2$—$H_2O$, EtOH, 100°; (e) R⁴—X (X=halo).

Scheme 3 above shows a general route for the preparation of compounds of formula I wherein $R^1$ is $-(L)_mAr^1$ and m is zero, X is oxygen, and $R^4$ is R. Intermediate 4 is prepared from compound 2 as previously described in Scheme 1. Compound 4 is converted to chloride 16 with $POCl_3$ according to the method of Schober et al., *J. Het. Chem.*, 27, pp. 471-477 (1990). Hydroxy pyrazolo-pyridazine 17 is prepared according to the method of Patel et al., *Indian J. Chem.*, 26B, pp. 733-744 (1989) and finally alkylation of 17 is accomplished with R⁴ halide according to the method of Oelschlager, et al., *Arch. Pharm.*, 319, pp. 939-944 (1986) or Boananomi et al., *Farmaco*, 32, pp. 490-501 (1977) or Ardakani, et al., *J. Chem. Soc. Perkin Trans.*, 1, pp. 2501-2506 (1983).

Scheme 4:

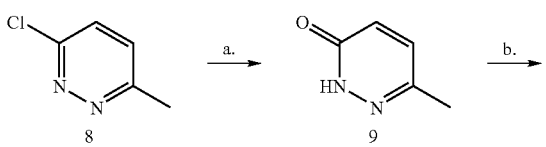

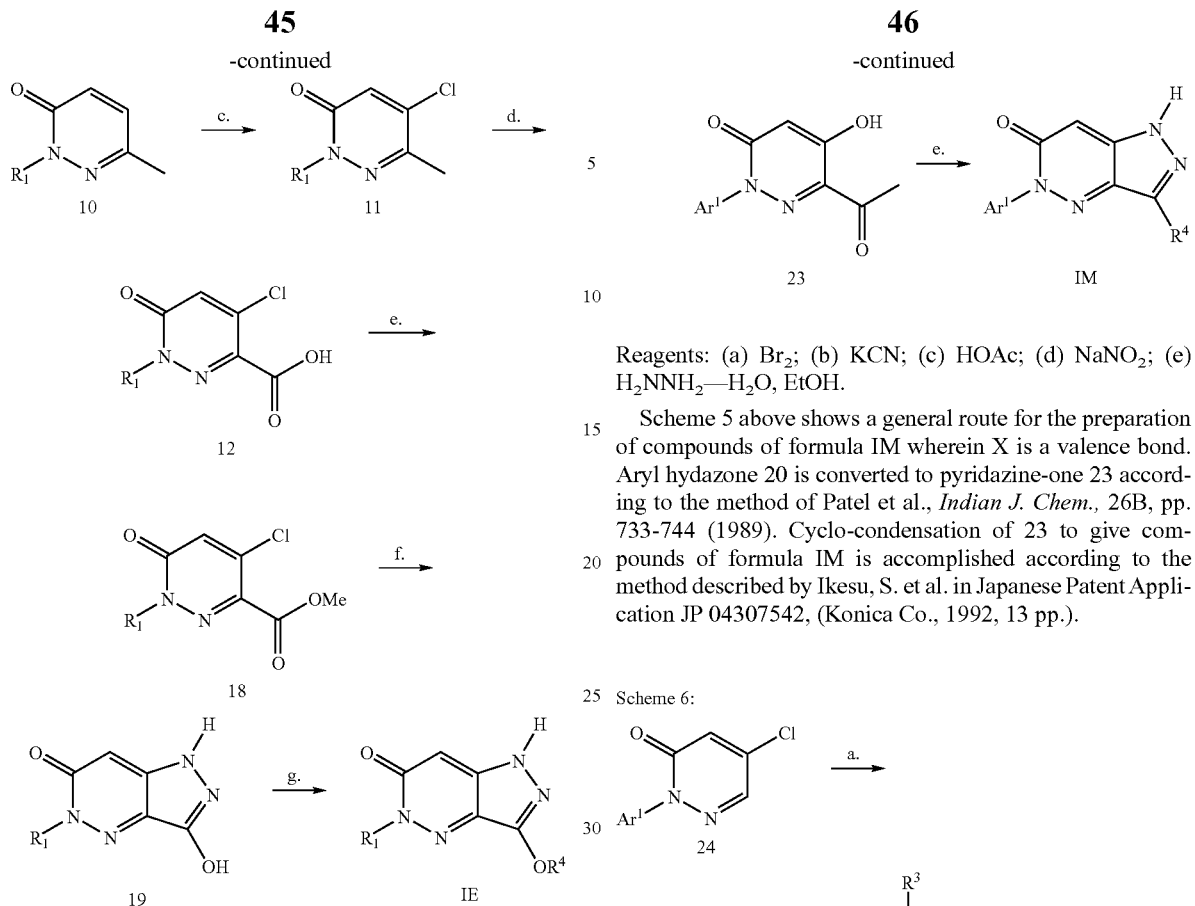

Reagents: (a) Br$_2$; (b) KCN; (c) HOAc; (d) NaNO$_2$; (e) H$_2$NNH$_2$—H$_2$O, EtOH.

Scheme 5 above shows a general route for the preparation of compounds of formula IM wherein X is a valence bond. Aryl hydazone 20 is converted to pyridazine-one 23 according to the method of Patel et al., *Indian J. Chem.*, 26B, pp. 733-744 (1989). Cyclo-condensation of 23 to give compounds of formula IM is accomplished according to the method described by Ikesu, S. et al. in Japanese Patent Application JP 04307542, (Konica Co., 1992, 13 pp.).

Scheme 6:

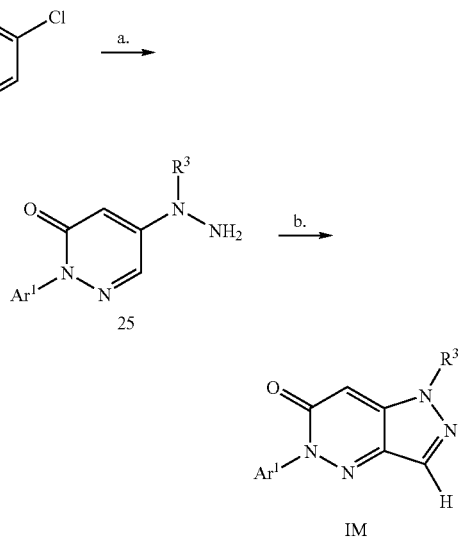

Reagents: (a) R$^3$HNNH$_2$; (b) (CH$_3$)$_2$NCH(OCH$_3$)$_2$

Scheme 6 above shows a general route for the preparation of certain compounds of formula IM wherein X is a valence bond and R$^4$ is hydrogen. Compounds of formula IJ can be prepared from compound 24 according to the methods described by Anderson, P. L. in U.S. Pat. No. 4,004,009 (Sandoz, Inc. 1977, 5 pp.).

Reagents: (a) HNO$_3$; (b) R$^1$(L)$_m$-X (X=halo); (c) Cl$_2$; (d) K$_2$Cr$_2$O$_7$; (e) MeOH; HCl (f) H$_2$NNH$_2$—H$_2$O, EtOH; (g) R$^4$—X (X=halo).

Scheme 4 above shows a general route for preparing compounds of formula IE wherein R$^1$ is (L)$_m$R, and X is oxygen. Intermediate 12 is prepared according to the method described in Scheme 1. Acid 12 is converted to methyl ester 18 via Fisher esterification and then cyclocondensed with hydrazine hydrate according to the method described in Scheme 3 to give hydroxy pyrazolo-pyridazine 19. O-alkylation is accomplished with R$^4$ halide according to the methods described above in Scheme 3.

Scheme 5:

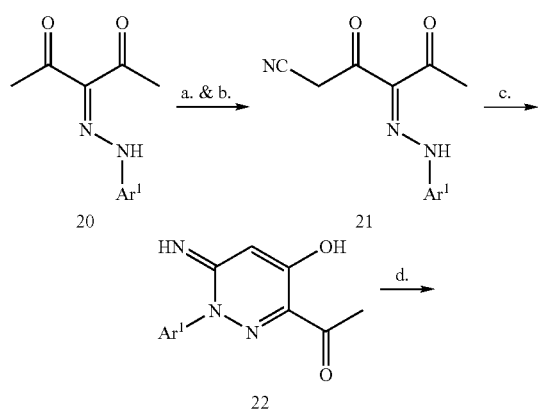

Scheme 7:

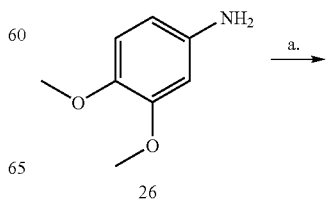

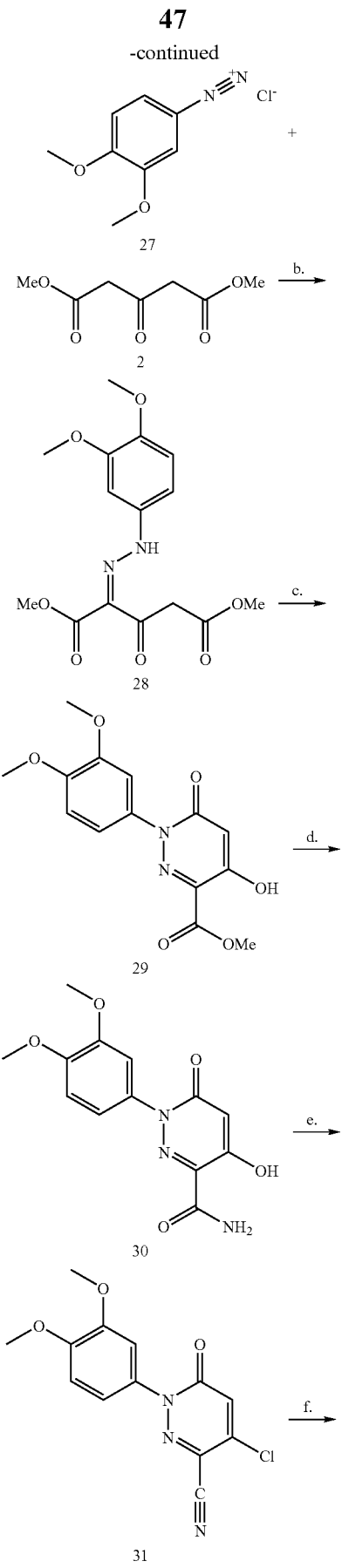
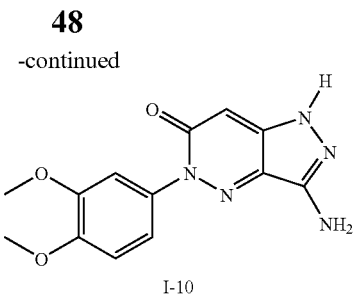

Reagents: (a) NaNO$_2$, HCl, H$_2$O; (b) NaOAc, EtOH, H$_2$O; (c) dichlorobenzene, reflux; (d) 7N NH$_3$ in MeOH; (e) POCl$_3$, CH$_3$CN, reflux; (f) H$_2$NNH$_2$—H$_2$O, EtOH, 100°.

Scheme 7 above shows a synthetic route for the preparation of compound I-10 of the present invention from commercial aniline 26 using the method described by Schober et al. in *J. Heterocyclic Chem.*, 26, pp. 169-176 (1989) and the method described above in Scheme 1.

Although certain exemplary embodiments are depicted and described above and herein, it will be appreciated that a compounds of the invention can be prepared according to the methods described generally above using appropriate starting materials by methods generally available to one of ordinary skill in the art.

The activity of a compound utilized in this invention as an inhibitor of GSK-3 may be assayed in vitro, in vivo or in a cell line. In vitro assays include assays that determine inhibition of either the phosphorylation activity or ATPase activity of activated GSK-3. Alternate in vitro assays quantitate the ability of the inhibitor to bind to GSK-3. Inhibitor binding may be measured by radiolabelling the inhibitor prior to binding, isolating the inhibitor/GSK-3 complex and determining the amount of radiolabel bound. Alternatively, inhibitor binding may be determined by running a competition experiment where new inhibitors are incubated with GSK-3 bound to known radioligands.

According to another embodiment, the invention provides a composition comprising a compound of this invention or a pharmaceutically acceptable salt thereof and a pharmaceutically acceptable carrier, adjuvant, or vehicle. The amount of compound in the compositions of this invention is such that is effective to detectably inhibit a protein kinase, particularly GSK-3, in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "detectably inhibit", as used herein means a measurable change in GSK-3 activity between a sample comprising said composition and GSK-3 kinase and an equivalent sample comprising GSK-3 kinase in the absence of said composition.

A "pharmaceutically acceptable salt" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite of a compound of the present invention, or residue thereof, is also an inhibitor of GSK-3 kinase.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N+(C1-4 alkyl)4 salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention.

For example, neurotrophic factors or other agents for treating neurological or neurodegenerative disorders may be combined with the compounds of this invention to treat neurological and neurodegenerative disorders. Examples of known neurotrophic factors include, but are not limited to, acetylcholinesterase inhibitors, MAO inhibitors, interferons, anti-convulsants, ion channel blockers, riluzole, and anti-Parkinsonian agents.

Examples of known treatments for stroke include Activase®, a recombinant, or genetically engineered, tissue plasminogen activator (rt-PA), heparin, glutamate antagonists, calcium antagonists, opiate antagonists, GABA agonists and antioxidants.

Other examples of agents the compounds of this invention may also be combined with include, without limitation, anti-depressive agents, such as Zoloft®, Prozac®, Paxil®, and Buspar®; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating diabetes such as insulin, insulin analogues, alpha glucosidase inhibitors, biguanides, and insulin sensitizers; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

According to another embodiment, the present invention relates to administering to a patient an additional therapeutic agent selected from a treatment for Alzheimer's Disease (AD), a treatment for Parkinson's Disease, an agent for treating Multiple Sclerosis (MS), a treatment for asthma, an anti-inflammatory agent, an immunomodulatory or immunosuppressive agent, a neurotrophic factor, an agent for treating stroke, an agent for treating cardiovascular disease, an antidepressant, an anti-psychotic agent, or an agent for treating diabetes, wherein:

said additional therapeutic agent is appropriate for the disease being treated; and said additional therapeutic agent is administered together with said composition as a single dosage form or separately from said composition as part of a multiple dosage form.

According to another embodiment, the invention relates to a method of inhibiting GSK-3 kinase activity in a biological sample comprising the step of contacting said biological sample with a compound of this invention, or composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of GSK-3 kinase activity in a biological sample is useful for a variety of purposes which are known to one of skill in the art. Examples of such purposes include, but are not limited to, blood transfusion, organ-transplantation, biological specimen storage, and biological assays.

According to another embodiment, the invention relates to a method of inhibiting GSK-3 kinase activity in a patient comprising the step of administering to said patient a compound of this invention, or composition comprising said compound.

According to another embodiment, the invention provides a method for treating or lessening the severity of a GSK-3-mediated disease or condition in a patient comprising the step of administering to said patient a composition according to the present invention.

The term "GSK-3-mediated disease" as used herein, means any disease or other deleterious condition or disease in which GSK-3 is known to play a role. Such diseases or conditions include, without limitation, autoimmune disease, an inflammatory disease, a metabolic disorder, a psychiatric disorder, diabetes, an angiogenic disorder, tauopothy, a neurological or neurodegenerative disorder, a spinal cord injury, glaucoma, baldness, or a cardiovascular disease.

According to another embodiment, the present invention relates to a method for treating or lessening the severity of a disease, disorder, or condition selected from an autoimmune disease, an inflammatory disease, a metabolic disorder, a psychiatric disorder, diabetes, an angiogenic disorder, tauopothy, a neurological or neurodegenerative disorder, a spinal cord injury, glaucoma, baldness, or a cardiovascular disease, in a patient in need thereof, comprising administering to said patient a compound of the present invention or composition thereof.

According to another embodiment, the present invention relates to a method for treating or lessening the severity of a disease or condition selected from allergy, asthma, diabetes, Alzheimer's disease, Huntington's disease, Parkinson's disease, AIDS-associated dementia, amyotrophic lateral sclerosis (ALS, Lou Gehrig's disease), multiple sclerosis (MS), an injury due to head trauma, schizophrenia, anxiety, bipolar disorder, tauopothy, a spinal cord or peripheral nerve injury, myocardial infarction, cardiomyocyte hypertrophy, glaucoma, attention deficit disorder (ADD), depression, a sleep disorder, reperfusion/ischemia, stroke, an angiogenic disorder, or baldness, wherein said method comprises administering to a patient in need thereof a compound of the present invention or composition thereof.

According to another embodiment, the method of the present invention relates to treating or lessening the severity of stroke.

According to another embodiment, the method of the present invention relates to treating or lessening the severity of Alzheimer's disease.

According to another embodiment, the method of the present invention relates to treating or lessening the severity of a neurodegenerative or neurological disorder.

According to another embodiment, the method of the present invention relates to decreasing sperm motility in a male patient.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another embodiment, includes a composition for coating an implantable device comprising a compound of the present invention as described generally above, and in classes and subclasses herein, and a carrier suitable for coating said implantable device. In still another embodiment, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof The coatings may optionally be further covered by a suitable topcoat of fluorosilicone, polysaccarides, polyethylene glycol, phospholipids or combinations thereof to impart controlled release characteristics in the composition.

In an alternate embodiment, the methods of this invention that utilize compositions that do not contain an additional therapeutic agent, comprise the additional step of separately administering to said patient an additional therapeutic agent. When these additional therapeutic agents are administered separately they may be administered to the patient prior to, sequentially with or following administration of the compositions of this invention.

In order that the invention described herein may be more fully understood, the following examples are set forth. It should be understood that these examples are for illustrative purposes only and are not to be construed as limiting this invention in any manner.

EXAMPLES $^1$H-NMR spectra were recorded at 500 MHz using a Bruker AMX 500 instrument. Mass spec. samples were analyzed on a MicroMass ZQ or Quattro II mass spectrometer operated in single MS mode with electrospray ionization. Samples were introduced into the mass spectrometer using chromatography. Mobile phase for all mass spec. analysis consisted of acetonitrile-water mixtures with 0.2% formic acid as a modifier.

As used herein, the term "$R_t$(min)" refers to the HPLC retention time, in minutes, associated with the compounds of this invention obtained from the mass spec. analysis.

Chemical naming for selected compounds herein was accomplished using the naming program provided by CambridgeSoft Corporations ChemDraw Ultra®, version 7.0.1

Example 1

2-[(3,4-Dimethoxy-phenyl)-hydrazono]-3-oxo-pentanedioic acid dimethyl ester (28)

A mixture of 2.5 ml of concentrated HCl, 5 ml of $H_2O$, and 5.523 mmoles of aniline (26) was treated with a solution of sodium nitrite 381 mg (5.52 mmoles) in 5 ml of water in an ice bath. This reaction was stirred for two hours to give crude diazonium chloride (27) which was not isolated. The crude diazonium salt solution was poured into a mixture of 961 mg of dimethyl acetonedicarboxylate (2) in 3 ml of ethanol and 3 g of sodium acetate in 10 ml of water with vigorous stirring. Product precipitated immediately. The reaction was allowed to stir for an additional 2 hours, then filtered and dried to give 1.363 g of the desired hydrazone (28) as a solid. MS$^+$: m/e=339.1 (M+H).

Example 2

1-(3,4-Dimethoxy-phenyl)-4-hydroxy-6-oxo-1,6-dihydro-pyridazine-3-carboxylic acid methyl ester (29)

The hydrazone (28) (500 mg) was dissolved in dichlorobenzene and heated to reflux in a sealed tube for 4 hours. The reaction was allowed to cool and cyclohexane was added dropwise to crystallize the desired product. Filtration and drying in vacuo yielded the desired dihydropyridazine ester (29) (295 mg) as a solid. MS$^+$: m/e=307.0 (M+H).

Example 3

1-(3,4-Dimethoxy-phenyl)-4-hydroxy-6-oxo-1,6-dihydro-pyridazine-3-carboxylic acid amide (30)

The pyridazine (29) (295 mg) was dissolved in 3 ml of 7N $NH_3$ in methanol and heated to reflux in a sealed tube for 4 hours. The reaction was allowed to cool, neutralized with acetic acid, and concentrated to dryness to give 266 mg of desired amide (30) as a solid. MS$^+$: m/e=292.0 (M+H).

Example 4

4-Chloro-1-(3,4-dimethoxy-phenyl)-6-oxo-1,6-dihydro-pyridazine-3-carbonitrile (31)

The starting amide (30) (190 mg) was dissolved in 1 ml of $CH_3CN$, treated with 1 ml of phosphorus oxychloride, and heated to reflux. After 18-20 hours the reaction was complete by HPLC. The reaction mixture was poured into ice and stirred for one hour. The product was extracted with ethyl acetate, the organic phase dried over magnesium sulfate, filtered, and concentrated to dryness. This material was then purified by normal phase column $SiO_2$ chromatography affording 90 mg of desired nitrile chloride (31) as a solid. MS$^+$: m/e=292.0 (M+H), $^1$H-NMR (500 MHz, MeOH-d$_4$): δ 7.40 (s, 1H), 7.18 (s, 1H), 7.12 (d, 1H), 7.08 (d, 1H), 3.90 (s, 3H), 3.85 (s, 3H), ppm.

Example 5

3-Amino-5-(3,4-dimethoxy-phenyl)-1,5-dihydro-pyrazolo[4,3-c]pyridazine-6-one (I-10)

The starting chloride (31) (190 mg) was dissolved in 500 μl of ethanol. 5 equivalents of hydrazine hydrate were added and the reaction mixture heated in a sealed tube at 100° C. for 18 hours. HPLC showed the reaction to be complete. The reaction was concentrated to dryness and purified by normal phase $SiO_2$ chromatography eluting with (1:1) ethyl acetate-hexanes going to 100% ethyl acetate to give after drying 25 mg of desired product (I-10) as a solid. MS$^+$: m/e=288.0 (M+H)$^+$, $^1$H-NMR (500 MHz, MeOH-d$_4$): δ 7.17 (s, 1H), 7.11 (d, 1H), 7.07 (d, 1H), 6.37 (s, 1H), 3.90 (s, 3H), ppm.

Example 6

5-(4-Methoxy-phenyl)-3-(pyrimidin-2-ylamino)-1,5-dihydro-pyrazolo[4,3-c]pyridazin-6-one (I-17)

To 3-amino-5-(4-methoxy-phenyl)-1,5-dihydro-pyrazolo[4,3-c]pyridazin-6-one (purchased from Bionet, 67.6 mg, 0.2628 mmoles) in N-methylpyrrolidinone (263 uL) was added 2-chloro-pyrimidine (15.1 mg, 0.5 eq). The reaction was stirred for 5 hours at 130° C. to give crude desired product as evidenced by mass spectrometry. The reaction was diluted with methanol (2 ml) and purified by reverse phase chromatography to give 25 mg (28%) of pure 5-(4-methoxy-phenyl)-3-(pyrimidin-2-ylamino)-1,5-dihydro-pyrazolo[4,3-c]pyridazin-6-one (I-17) as a solid. LC/MS: t$_{ret}$=2.13 min, M+H$^-$=336.1.

Table 2 below depicts exemplary mass spectral and $^1$H-NMR data for certain compounds of this invention:

TABLE 2

| Compound | Mass Spec. (M + H)$^+$ | R$_t$(min) | $^1$H-NMR |
|---|---|---|---|
| I-1 | 258.0 | 1.59 | Methanol-d4: δ 7.4 (m, 1H), 7.12 (m, 2H), 7.04 (dd, 1H), 6.35 (s, 1H), 3.33 (s, 3H) ppm. |
| I-2 | 228.0 | 1.38 | Methanol-d4: δ 7.6-7.4 (m, 5H), 6.35 (s, 1H) ppm. |
| I-3 | 296.0 | 2.1 | Methanol-d4: δ 7.72 (m, 1H), 7.52 (m, 2H), 6.35 (s, 1H) ppm. |
| I-4 | 320.1 | 2.63 | Methanol-d4: δ 7.54 (d, 2H), 7.38 (t, 2H), 7.16 (t, 1H), 7.08 (m, 4H), 6.35 (s, 1H) ppm. |
| I-5 | 242.1 | 1.80 | DMSO-d6: δ 11.17 (s, 1H), 7.41 (d, 2H), 7.28 (d, 2H), 6.18 (s, 1H), 6.1 (s, 2H), 2.36 (s, 3H) ppm. |
| I-6 | 484.1 | 2.17 | |
| I-7 | 273.0 | 1.59 | DMSO-d6: δ 11.2 (s, 1H), 8.51 (s, 1H), 8.3 (d, 1H), 8.13 (d, 1H), 7.82 (t, 1H), 6.25 (s, 1H), 6.18 (s, 2H) ppm. |
| I-8 | 262.0 | 1.80 | DMSO-d6: δ 11.22 (s, 1H), 7.65-7.5 (m, 3H), 6.2-6.05 (m, 3H) ppm. |
| I-9 | 307.0 | | DMSO-d6: δ 11.25 (s, 1H), 8.03 (s, 1H), 7.9 (d, 1H), 7.82 (d, 1H), 7.71 (m, 1H), 7.53 (m, 2H), 6.22 (s, 1H), 6.15 (s, 2H) ppm. |
| I-10 | 288.0 | 1.21 | Methanol-d4: δ 7.17 (d, 1H), 7.11 (d, 1H), 7.07 (s, 1H), 6.37 (s, 1H), 3.9 (s, 3H), 3.85 (s, 3H) ppm. |
| I-11 | 336.1 | 2.09 | |
| I-12 | 374.1 | 2.58 | |
| I-13 | 374.2 | 2.67 | |
| I-14 | 398.2 | 3.03 | |
| I-15 | 262.0 | 1.17 | DMSO-d6: δ 11.2 (s, 1H), 7.68 (dd, 1H), 7.61 (dd, 1H), 7.53 (m, 2H), 6.22 (s, 1H), 6.16 (s, 2H) ppm. |
| I-16 | 258.1 | 1.05 | DMSO-d6: δ 11.2 (s, 1H), 7.46 (t, 1H), 7.33 (d, 1H), 7.2 (d, 1H), 7.07 (t, 1H), 6.4-6.0 (bs, 2H), 6.14 (s, 1H), 3.73 (s, 3H) ppm. |
| I-17 | 336.1 | 2.13 | |
| I-18 | 273.0 | 1.63 | DMSO-d6: δ 11.25 (s, 1H), 8.39 (d, 2H), 7.95 (d, 2H), 6.2 (m, 3H) ppm. |

Example 7

Inhibition of GSK-3

Compounds were screened for their ability to inhibit GSK-3β (AA 1-420) activity using a standard coupled enzyme system (Fox et al. *Protein Sci.* 7, p. 2249 (1998)). Reactions were carried out in a solution containing 100 mM HEPES (pH 7.5), 10 mM MgCl$_2$, 25 mM NaCl, 300 μM NADH, 1 mM DTT and 1.5% DMSO. Final substrate concentrations in the assay were 20 μM ATP (Sigma Chemicals, St Louis, Mo.) and 300 μM peptide (American Peptide, Sunnyvale, Calif.). Reactions were carried out at 30° C. and 20 nM GSK-3β. Final concentrations of the components of the coupled enzyme system were 2.5 mM phosphoenolpyruvate, 300 μM NADH, 30 μg/ml pyruvate kinase and 10 μg/ml lactate dehydrogenase.

An assay stock buffer solution was prepared containing all of the reagents listed above with the exception of ATP and the test compound of interest. The assay stock buffer solution (175 μl) was incubated in a 96 well plate with 5 μl of the test compound of interest at final concentrations spanning 0.002 μM to 30 μM at 30° C. for 10 min. Typically, a 12 point titration was conducted by preparing serial dilutions (from 10 mM compound stocks) with DMSO of the test compounds in daughter plates. The reaction was initiated by the addition of 20 μl of ATP (final concentration 20 μM). Rates of reaction were obtained using a Molecular Devices Spectramax plate reader (Sunnyvale, Calif.) over 10 min at 30° C. The K$_i$ values were determined from the rate data as a function of inhibitor concentration.

The following compounds were shown to have K$_i$ values less than 4.0 μM for GSK-3: I-1, I-2, I-4, I-5, I-6, I-7, I-8, and I-9.

We claim:
1. A compound of formula I:

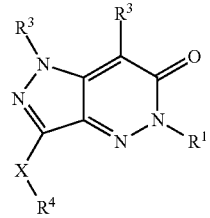

or a pharmaceutically acceptable salt or mixtures thereof, wherein $R^1$ is selected from $-(L)_mR$, $-(L)_mAr^1$, or $-(L)_mCy^1$; L is an optionally substituted $C_{1-6}$ alkylidene chain wherein up to two non-adjacent methylene units of L are optionally replaced by O, NR, NRCO, NRCS, NRCONR, NRCSNR, NRCO$_2$, CO, CO$_2$, CONR, CSNR, OC(O)NR, SO$_2$, SO$_2$NR, NRSO$_2$, NRSO$_2$NR, C(O)C(O), or C(O)CH$_2$C(O); m is 0 or 1; $Ar^1$ is an optionally substituted aryl group selected from a 3-8 membered monocyclic or an 8-10 membered bicyclic ring having 0-5 heteroatoms independently selected from nitrogen, oxygen, or sulfur; and $Cy^1$ is an optionally substituted group selected from a 3-7-membered saturated or partially unsaturated monocyclic ring having 0-3 heteroatoms independently selected from nitrogen, oxygen, or sulfur, or an 8-10-membered saturated or partially unsaturated bicyclic ring system having 0-5 heteroatoms independently selected from nitrogen, oxygen, or sulfur, wherein $Ar^1$ and $Cy^1$ are each independently optionally substituted with up to five substituents selected from $Z-R^Y$; wherein Z is a bond or is a $C_1$-$C_6$ alkylidene chain wherein up to two non-adjacent methylene units of Z are optionally replaced by CO, CO$_2$, COCO, CONR, CSNR, OCONR, NRNR, NRNRCO, NRCO, NRCS, NRCO$_2$, NRCONR, NRCSNR, SO, SO$_2$, NRSO$_2$, SO$_2$NR, NRSO$_2$NR, O, S, or NR; and each occurrence of $R^Y$ is independently selected from R', halogen, NO$_2$, CN, OR', SR', N(R')$_2$, NR'C(O)R', NR'C(S)R', NR'C(O)N(R')$_2$, NR'C(S)N(R')$_2$, NR'CO$_2$R', C(O)R', CO$_2$R', OC(O)R', C(O)N(R')$_2$, C(S)N(R')$_2$, OC(O)N(R')$_2$, SOR', SO$_2$R', SO$_2$N(R')$_2$, NR'SO$_2$R', NR'SO$_2$N(R')$_2$, C(O)C(O)R', or C(O)CH$_2$C(O)R';

$R^2$ is selected from halogen, NO$_2$, CN, —SR', —N(R)$_2$, -(T)$_n$R, or -(T)$_n$Ar$^2$ wherein T is an optionally substituted $C_{1-4}$ alkylidene chain wherein up to two non-adjacent methylene units of T are optionally replaced by O, NR, NRCO, NRCS, NRCONR, NRCSNR, NRCO$_2$, CO, CO$_2$, CONR, CSNR, OC(O)NR, SO$_2$, SO$_2$NR, NRSO$_2$, NRSO$_2$NR, C(O)C(O), or C(O)CH$_2$C(O); n is 0 or 1; $Ar^2$ is an optionally substituted aryl group selected from a 5-6 membered monocyclic or an 8-10 membered bicyclic ring having 0-5 heteroatoms independently selected from nitrogen, oxygen, or sulfur wherein $Ar^2$ is independently optionally substituted with up to five substituents selected from Q-$R^X$; wherein Q is a bond or is a $C_1$-$C_6$ alkylidene chain wherein up to two non-adjacent methylene units of Q are optionally replaced by CO, CO$_2$, COCO, CONR, CSNR, OCONR, NRNR, NRNRCO, NRCO, NRCS, NRCO$_2$, NRCONR, NRCSNR, SO, SO$_2$, NRSO$_2$, SO$_2$NR, NRSO$_2$NR, O, S, or NR; and each occurrence of $R^X$ is independently selected from R', halogen, NO$_2$, CN, OR', SR', N(R')$_2$, NR'C(O)R', NR'C(S)R', NR'C(O)N(R')$_2$, NR'C(S)N(R')$_2$, NR'CO$_2$R', C(O)R', CO$_2$R', OC(O)R', C(O)N(R')$_2$, C(S)N(R')$_2$, OC(O)N(R')$_2$, SOR', SO$_2$R', SO$_2$N(R')$_2$, NR'SO$_2$R', NR'SO$_2$N(R')$_2$, C(O)C(O)R', or C(O)CH$_2$C(O)R';

$R^3$ is hydrogen or an optionally substituted $C_{1-4}$ aliphatic group;

X is selected from a valence bond, O, S, or NR;

$R^4$ is $Ar^3$;

$Ar^3$ is an optionally substituted aryl group selected from a 3-8 membered monocyclic or an 8-10 membered bicyclic ring having 0-5 heteroatoms independently selected from nitrogen, oxygen, or sulfur; wherein $Ar^3$ is optionally substituted with up to five substituents selected from $Y-R^Z$; wherein Y is a bond or is a $C_1$-$C_6$ alkylidene chain wherein up to two non-adjacent methylene units of Y are optionally replaced by CO, CO$_2$, COCO, CONR, CSNR, OCONR, NRNR, NRNRCO, NRCO, NRCS, NRCO$_2$, NRCONR, NRCSNR, SO, SO$_2$, NRSO$_2$, SO$_2$NR, NRSO$_2$NR, O, S, or NR; and each occurrence of $R^Z$ is independently selected from R', halogen, NO$_2$, CN, OR', SR', N(R')$_2$, NR'C(O)R', NR'C(S)R', NR'C(O)N(R')$_2$, NR'C(S)N(R')$_2$, NR'CO$_2$R', C(O)R', CO$_2$R', OC(O)R', C(O)N(R')$_2$, C(S)N(R')$_2$, OC(O)N(R')$_2$, SOR', SO$_2$R', SO$_2$N(R')$_2$, NR'SO$_2$R', NR'SO$_2$N(R')$_2$, C(O)C(O)R', or C(O)CH$_2$C(O)R'; or wherein $R^4$ and R, taken together with the nitrogen form an optionally substituted 5-8 membered heterocyclyl or heteroaryl ring having 1-3 heteroatoms independently selected from nitrogen, oxygen, or sulfur;

each occurrence of R is independently selected from hydrogen or an optionally substituted $C_{1-6}$ aliphatic group, or two R on the same nitrogen are taken together with the nitrogen to form a 5-8 membered heterocyclyl or heteroaryl ring having 1-3 heteroatoms independently selected from nitrogen, oxygen, or sulfur; and each occurrence of R' is independently selected from hydrogen or an optionally substituted group selected from $C_{1-6}$ aliphatic, $C_{6-10}$ aryl, a heteroaryl ring having 5-10 ring atoms, or a heterocyclyl ring having 3-10 ring atoms, or wherein two R on the same nitrogen are taken together with the nitrogen to form a 5-8 membered heterocyclyl or heteroaryl ring having 1-3 heteroatoms independently selected from nitrogen, oxygen, or sulfur, provided that:
b) when X is NR; R and $R^3$ are each hydrogen; $R^2$ is -(T)$_n$R wherein n is 0 and R is hydrogen; $R^4$ is 2-phenyl-4-quinazolinyl; and $R^1$ is -(L)$_m$Ar$^1$ wherein m is 0; then $Ar^1$ is not:
  i) phenyl, 3-OMe phenyl, 4-OMe phenyl, 2,4-diCl phenyl, 4-Cl phenyl, 3-CF$_3$ phenyl, or 4-OPh phenyl;
c) when X is NR; R and $R^3$ are each hydrogen; $R^2$ is -(T)$_n$R wherein n is 0 and R is hydrogen; $R^4$ is 2-(2-trifluoromethyl-phenyl)-4-quinazolinyl; and $R^1$ is -(L)$_m$Ar$^1$ wherein m is 0; then $Ar^1$ is not phenyl;
h) 2-[2,4-bis(1,1-dimethylpropyl)phenoxy]-N-[4-[5,6-dihydro-6-oxo-5-(2-pyridinyl)-1H-pyrazolo[4,3-c]pyridazin-3-yl]phenyl]-acetamide; and
  N-[4-[5-(4-chlorophenyl)-5,6-dihydro-6-oxo-1H-pyrazolo[4,3-c]pyridazin-3-yl]phenyl]-2-[4-(1,1,3,3-tetramethylbutyl)phenoxy]-butanamide are both excluded.

2. The compound according to claim 1, wherein $R^1$ is $-(L)_m Ar^1$ and $Ar^1$ is selected from one of the following groups:
1-1
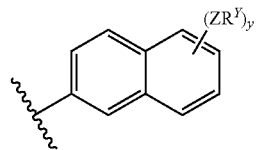
1-2
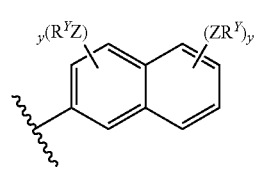
1-3
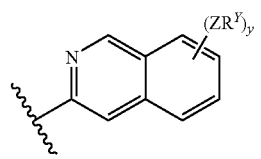
1-4
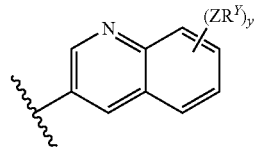
1-5
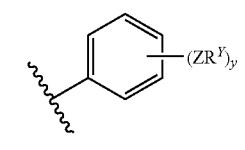
1-6
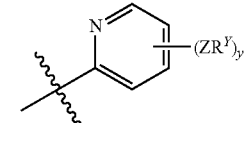
1-7
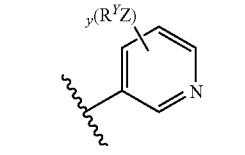
1-8
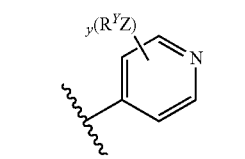
1-9
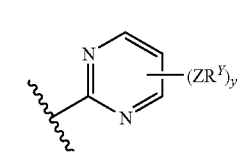
-continued
1-10
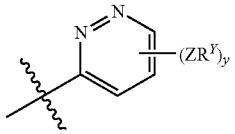
1-11
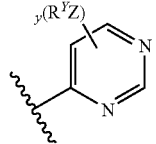
1-12
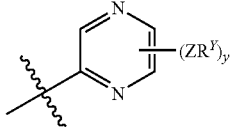
1-13
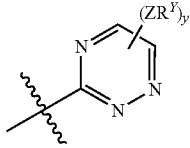
1-14
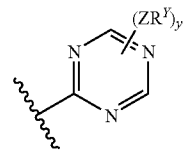
1-15
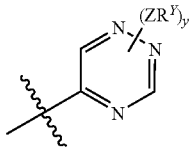
1-16
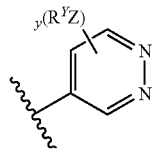
1-17
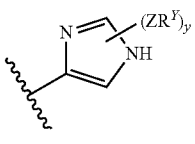
1-18
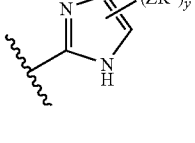
1-19
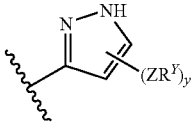

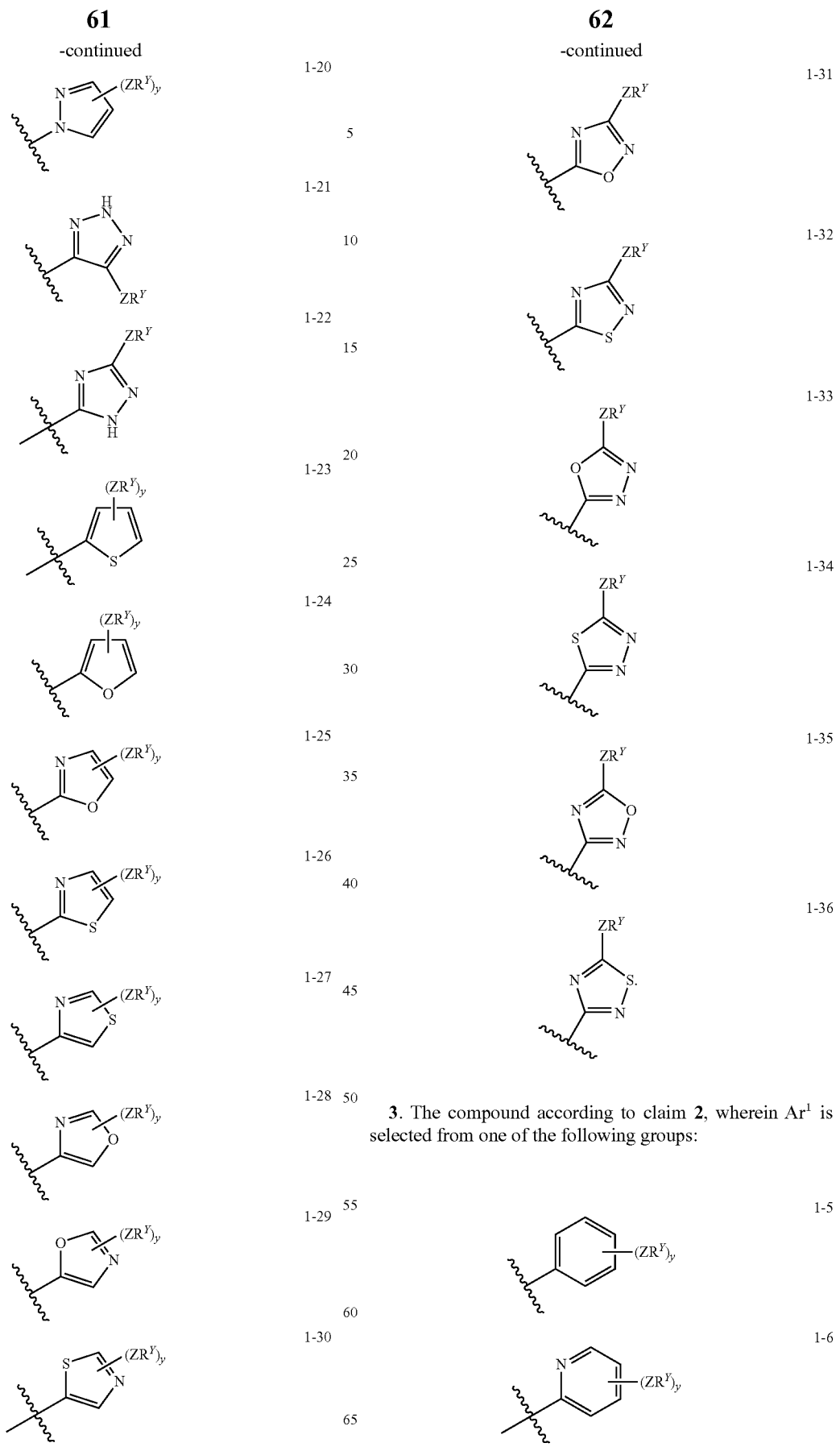
3. The compound according to claim 2, wherein Ar¹ is selected from one of the following groups:

1-7
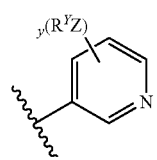
1-8
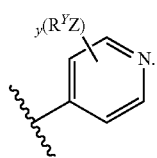
4. The compound according to claim 3, wherein Ar¹ is phenyl with 0-5 occurrences of ZR$^Y$ and compounds have the formula IA-1-5:
IA-1-5
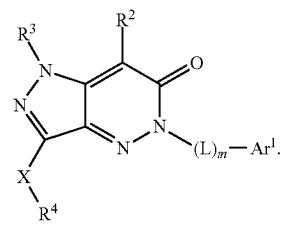
5. The compound according to claim 1, wherein R¹ is -(L)$_m$-Cy¹ and compounds have the formula IA-2:
IA-2
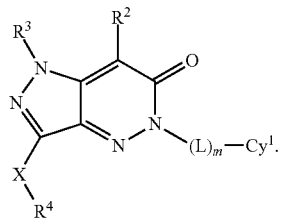
6. The compound according to claim 5, wherein Cy¹ is selected from one of the following groups:
2-1
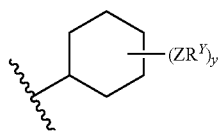
2-2
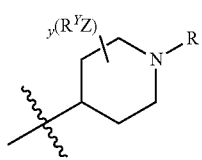
2-3
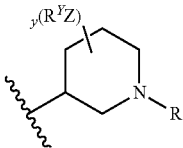
2-4
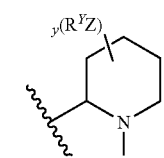
2-5
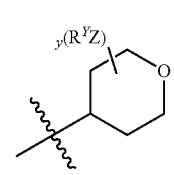
2-6
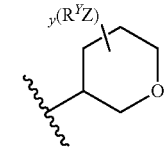
2-7
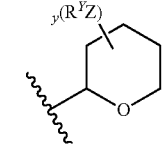
2-8
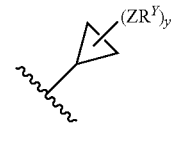
2-9
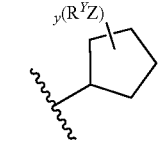
2-10
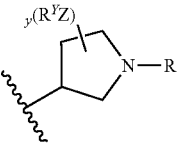
2-11
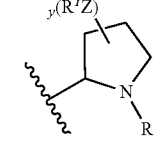
2-12
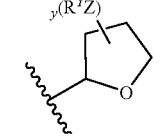

2-13

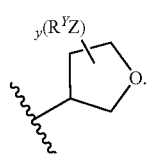

7. The compound according to claim 2, wherein L is an optionally substituted $C_{1-6}$ straight or branched alkylidene chain wherein one methylene unit of L is optionally replaced by O, NR, NRCO, NRCS, NRCONR, NRCSNR, NRCO$_2$, CO, CO$_2$, CONR, CSNR, OC(O)NR, SO$_2$, SO$_2$NR, NRSO$_2$, NRSO$_2$NR, C(O)C(O), or C(O)CH$_2$C(O) and m is 1.

8. The compound according to claim 1, wherein $R^1$ is $-(L)_mR$, L is an optionally substituted $C_{1-6}$ straight or branched alkylidene chain wherein one methylene unit of L is optionally replaced by O, NR, NRCO, NRCS, NRCONR, NRCSNR, NRCO$_2$, CO, CO$_2$, CONR, CSNR, OC(O)NR, SO$_2$, SO$_2$NR, NRSO$_2$, NRSO$_2$NR, C(O)C(O), or C(O)CH$_2$C(O), R is an optionally substituted $C_{1-6}$ aliphatic group and m is 1.

9. The compound according to claim 1, wherein $R^2$ is selected from $-N(R)_2$, or $-(T)_nR$, wherein n is 0, and R is selected from hydrogen or an optionally substituted $C_{1-6}$ aliphatic group.

10. The compound according to claim 1, wherein $R^3$ is hydrogen, methyl, ethyl, propyl, or isopropyl.

11. The compound according to claim 1, wherein X is NR, R is hydrogen, and compounds have the formula ID:

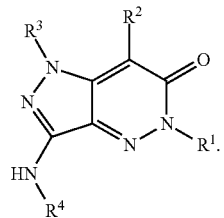

ID

12. The compound according to claim 1 or claim 4, wherein $Ar^3$ is selected from one of the following groups:

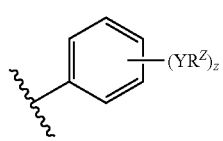

1-5-a

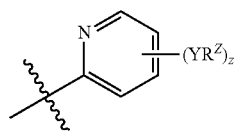

1-6-a

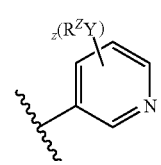

1-7-a

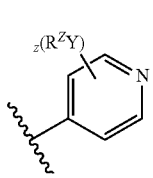

1-8-a

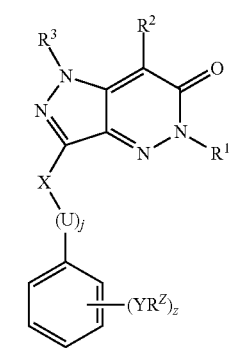

1-9-a 1-37

13. The compound according to claim 1, having one of the following formulas:

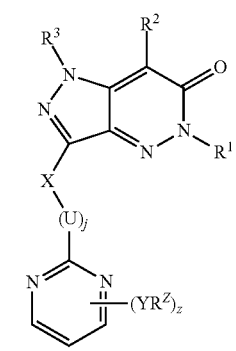

IE

IF

IG

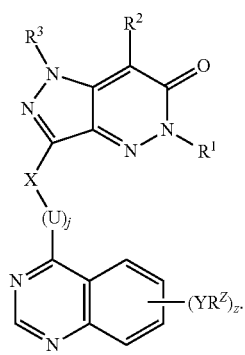

14. The compound according to claim 1, wherein y is 0, and Ar¹ is unsubstituted.

15. The compound according to claim 1, wherein $ZR^Y$ and $YR^Z$ groups are each independently halogen, NO₂, CN, or an optionally substituted group selected from $C_{1-4}$ aliphatic, aryl, aralkyl, —N(R')₂, —CH₂N(R')₂, —OR', —CH₂OR', —SR', —CH₂SR', —COOR', or —S(O)₂N(R')₂.

16. The compound according to claim 1, wherein R¹ is -(L)$_m$Ar¹, m is 0 or 1, Ar¹ is phenyl optionally substituted with 0-5 occurrences of $ZR^Y$, and compounds have one of the following formulas IIA or IIA-1:

IIA

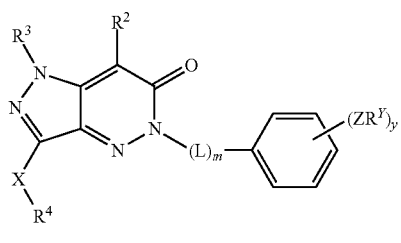

IIA-1

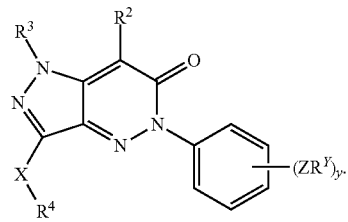

17. The compound according to claim 1, wherein R² is -(T)$_n$R, wherein n is 0 and R is hydrogen, R¹ is -(L)$_m$Ar¹, wherein m is 0 or 1, Ar¹ is phenyl optionally substituted with 0-3 occurrences of $ZR^Y$, and compounds have one of the following formulas IIB or IIB-1:

IIB

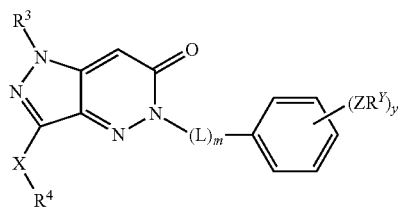

IIB-1

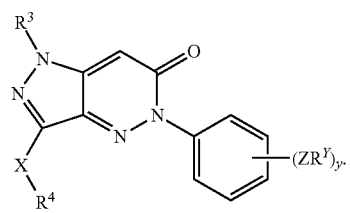

18. The compound according to claim 13, wherein Ar¹ is phenyl optionally substituted with 0-5 occurrences of $ZR^Y$ or wherein Ar¹ is pyridyl optionally substituted with 0-3 occurrences of $ZR^Y$.

19. The compound according to claim 18, wherein m is 0 or m is 1 and L is CH₂; y is 0-3; and each occurrence of $ZR^Y$ is independently halogen, NO₂, CN, or an optionally substituted group selected from $C_{1-4}$ aliphatic, aryl, aralkyl, —N(R')₂, —CH₂N(R')₂, —OR', —CH₂OR', —SR', —CH₂SR', —COOR', or —S(O)₂N(R')₂.

20. The compound according to claim 19, wherein each occurrence of $ZR^Y$ is independently Cl, CF₃, NO₂, —S(O)₂N(R')₂ or an optionally substituted group selected from $C_{1-4}$ alkoxy, phenyl, phenyloxy, benzyl, or benzyloxy.

21. The compound according to claim 12 or 13, wherein Ar³ is phenyl or quinazolyl optionally substituted with 0-5 occurrences of $YR^Z$ or wherein Ar³ is pyridyl or pyrimidinyl optionally substituted with 0-3 occurrences of $YR^Z$.

22. The compound according to claim 21, wherein j is 0 or 1 and U is CH₂; X is NH; m is 0 or 1 and L is CH₂; y is 0-3; and each occurrence of $YR^Z$ are each independently halogen, NO₂, CN, or an optionally substituted group selected from $C_{1-4}$ alkyl, aryl, aralkyl, —N(R')₂, —CH₂N(R')₂, —OR', —CH₂OR', —SR', —CH₂SR', —COOR', or —S(O)₂N(R')₂.

23. The compound according to claim 1, selected from one of the following compounds:

I-6

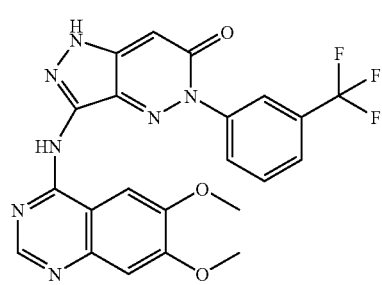 [SMILES: COc1cc2ncnc(Nc3n[nH]c4cc(=O)n(-c5cccc(C(F)(F)F)c5)nc34)c2cc1OC]

I-11

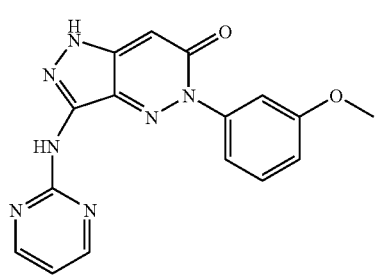 [SMILES: COc1cccc(-n2nc3c(Nc4ncccn4)n[nH]c3cc2=O)c1]

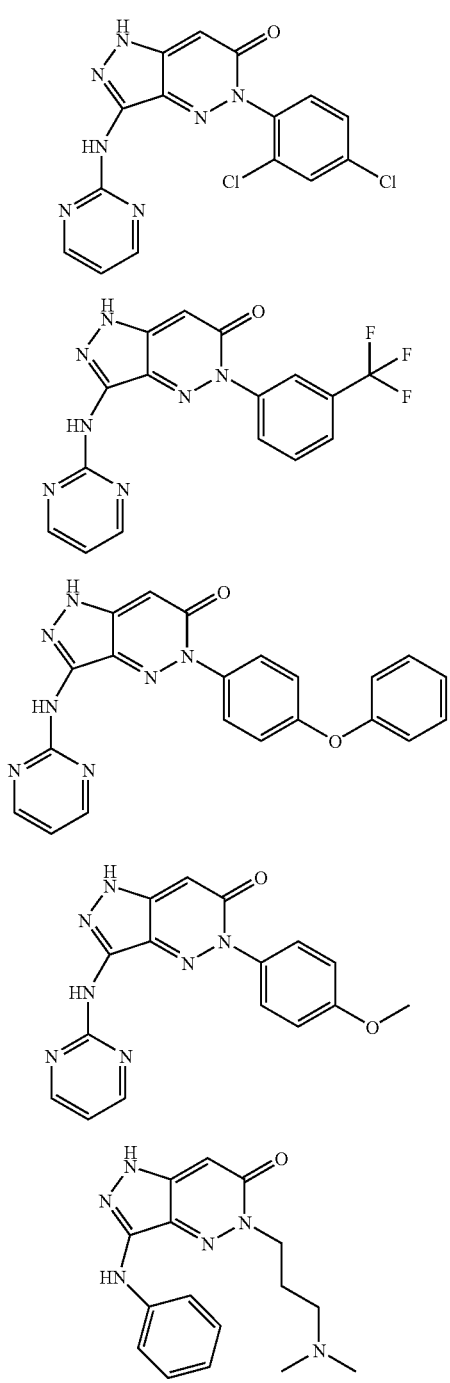
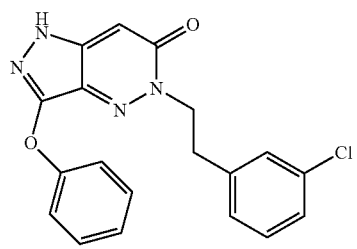 [SMILES: O=c1cc2[nH]nc(Oc3ccccc3)c2nn1CCc1cccc(Cl)c1]
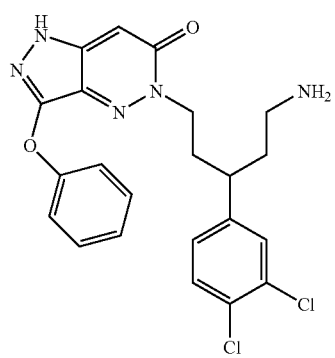 [SMILES: NCCC(CCn1nc2c(Oc3ccccc3)n[nH]c2cc1=O)c1ccc(Cl)c(Cl)c1]
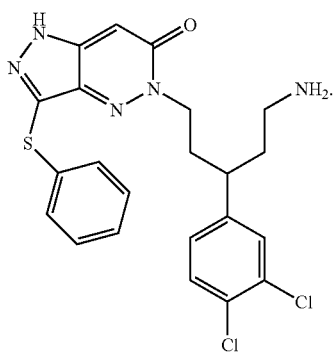
24. A pharmaceutically acceptable composition comprising a compound according to claim 1, and a pharmaceutically acceptable carrier, adjuvent, or vehicle.
25. A method of inhibiting GSK-3 kinase activity in a biological sample, comprising the step of contacting said biological sample with:
a) a composition according to claim 24; or
b) a compound according to claim 1.
* * * * *